US012780795B2

(12) United States Patent
Jeon et al.

(10) Patent No.: US 12,780,795 B2
(45) Date of Patent: Nov. 3, 2026

(54) CRYSTALLINE FORM OF TRICYCLIC DERIVATIVE COMPOUND, METHOD FOR PREPARING SAME, AND PHARMACEUTICAL COMPOSITION COMPRISING SAME

(71) Applicant: ONCONIC THERAPEUTICS INC., Seoul (KR)

(72) Inventors: Seong Hyeon Jeon, Suwon-si (KR); Jung Gi An, Yongin-si (KR); John Kim, Seoul (KR)

(73) Assignee: ONCONIC THERAPEUTICS INC., Seoul (KR)

( * ) Notice: Subject to any disclaimer, the term of this patent is extended or adjusted under 35 U.S.C. 154(b) by 363 days.

(21) Appl. No.: 18/561,962

(22) PCT Filed: May 18, 2022

(86) PCT No.: PCT/KR2022/007101

§ 371 (c)(1),
(2) Date: Nov. 17, 2023

(87) PCT Pub. No.: WO2022/245125

PCT Pub. Date: Nov. 24, 2022

(65) Prior Publication Data

US 2024/0246933 A1 Jul. 25, 2024

(30) Foreign Application Priority Data

May 18, 2021 (KR) ........................ 10-2021-0064416

(51) Int. Cl.

| | |
|---|---|
| ***C07D 401/12*** | (2006.01) |
| ***A61K 31/496*** | (2006.01) |
| ***A61P 9/00*** | (2006.01) |
| ***A61P 19/10*** | (2006.01) |
| ***A61P 25/28*** | (2006.01) |
| ***A61P 29/00*** | (2006.01) |
| ***A61P 35/00*** | (2006.01) |
| ***C07C 51/43*** | (2006.01) |
| ***C07C 55/22*** | (2006.01) |
| ***C07C 59/265*** | (2006.01) |
| ***C07D 471/04*** | (2006.01) |

(52) U.S. Cl.

CPC ............ *C07D 401/12* (2013.01); *C07C 51/43* (2013.01); *C07C 55/22* (2013.01); *C07B 2200/13* (2013.01)

(58) Field of Classification Search

None

See application file for complete search history.

(56) References Cited

U.S. PATENT DOCUMENTS

| | | | |
|---|---|---|---|
| 6,495,541 | B1 | 12/2002 | Webber et al. |
| 9,522,911 | B2 | 12/2016 | Ye et al. |
| 10,464,919 | B2 | 11/2019 | Lee et al. |
| 10,874,667 | B2 | 12/2020 | Fan et al. |
| 2014/0350007 | A1 | 11/2014 | Ye et al. |
| 2018/0162834 | A1 | 6/2018 | Lee et al. |
| 2018/0327851 | A1 | 11/2018 | Jin et al. |
| 2020/0354794 | A1 | 11/2020 | Jin et al. |

FOREIGN PATENT DOCUMENTS

| | | | |
|---|---|---|---|
| CA | 2 990 277 | A1 | 12/2016 |
| CN | 1342161 | A | 3/2002 |
| CN | 107849040 | A | 3/2018 |
| CN | 107955001 | A | 4/2018 |
| EP | 1 140 936 | B1 | 3/2004 |
| JP | 2018-521033 | A | 8/2018 |
| KR | 10-2013-0089089 | A | 8/2013 |
| KR | 10-2016-0144916 | A | 12/2016 |
| WO | 2008/067465 | A1 | 6/2008 |
| WO | 2011/153444 | A1 | 12/2011 |
| WO | 2013/115535 | A1 | 8/2013 |
| WO | 2016/200101 | A2 | 12/2016 |

OTHER PUBLICATIONS

Berge et al., Journal of Pharmaceutical Sciences, 1977, 66(1), 1-19.*

WO2016200101—machine-translation, 2026, machine translation of WO 2016200101.*

C. Alarccon De La Lastra, et al., "Poly(ADP-Ribose) Polymerase Inhibitors: New Pharmacological Functions and Potential Clinical Implications", Current Pharmaceutical Design, 2007, 13(9), 933-962.

Jean-Christophe Ame et al., "The PARP superfamily", BioEssays., 2004, 26(8), 882-893.

Helen E. Bryant et al., "Specific killing of BRCA2-deficient tumours with inhibitors of poly(ADP-ribose) polymerase", Nature, Apr. 14, 2005, vol. 434, 6 Pages.

(Continued)

*Primary Examiner* — Sun Jae Yoo

(74) *Attorney, Agent, or Firm* — Sughrue Mion, PLLC

(57) ABSTRACT

A novel crystalline form of a citrate of a tricyclic derivative compound represented by Formula 1, a method for preparing the crystalline form of the citrate, and a crystalline form of a tricyclic derivative compound represented by Formula 1, usefully used in the preparation of the crystalline form of the citrate.

Formula 1

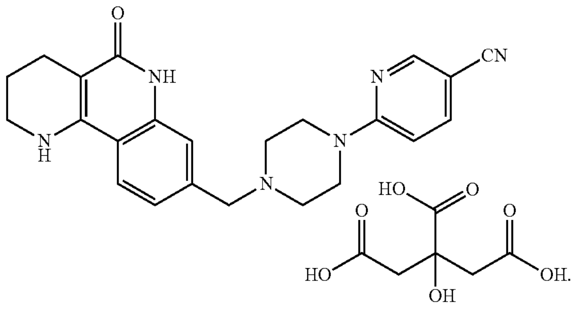

4 Claims, 18 Drawing Sheets

(56) References Cited

OTHER PUBLICATIONS

Nuala McCabe et al., "BRCA2-deficient CAPAN-1 cells are extremely sensitive to the inhibition of poly (ADP-ribose) polymerase: An issue of potency", Cancer Biology & Therapy, Sep. 2005, vol. 4 No. 9, pp. 934-936.
Lucio Tentori et al., "Chemopotentiation by PARP inhibitors in cancer therapy", Pharmacological Research, 2005, vol. 52, pp. 25-33.
Sheila J. Miknyoczki et al., "Chemopotentiation of Temozolomide, Irinotecan, and Cisplatin Activity by CEP-6800, a Poly(ADP-Ribose) Polymerase Inhibitor", Molecular Cancer Therapeutics, Apr. 2003, vol. 2, pp. 271-382.
Carol A. Delaney et al., "Potentiation of Temozolomide and Topotecan Growth Inhibition and Cytotoxicity by Novel Poly(adenosine Diphosphoribose) Polymerase Inhibitors in a Panel of Human Tumor Cell Lines", Clinical Cancer Research, Jul. 2000, vol. 6, pp. 2860-2867.
Matthias Endres et al., "Ischemic Brian Injury is Mediated by Activation of Poly(ADP-Ribose) Polymerase", Journal of Cerebral Blood Flow and Metabolism, 1997, vol. 17, pp. 1143-1151.
Irina G. Obrosova et al., "Oxidative-Nitrosative Stress and Poly(ADP-Ribose) Polymerase (PARP) Activation in Experimental Diabetic Neuropathy", Diabetes, Dec. 2005, vol. 54, pp. 3435-3441.
Barbara Lupo et al., "Inhibition of poly(ADP-ribosyl)ation in cancer: Old and new paradigms revisited" Biochimica et Biophysica Acta 1846, 2014, pp. 201-215.
Jenna L. Riffell et al., "Tankyrase-targeted therapeutics: expanding opportunities in PARP family", Nature Reviews, Drug Discovery, Dec 2012, vol. 11, pp. 923-936.
International Search Report for PCT/KR2022/007101 dated Aug. 26, 2022.
Written Opinion for PCT/KR2022/007101 dated Aug. 26, 2022.
Communication dated Nov. 28, 2024, issued in Canadian Application No. 3,219,303.
Office Action dated Feb. 18, 2026, issued in New Zealand Application No. 805567.
Zhenguo Gao et al., "Recent Developments in the Crystallization Process: Toward the Pharmaceutical Industry", Engineering, 2017, vol. 3, pp. 343-353.
Jaka Orehek et al., "Continuous Crystallization Processes in Pharmaceutical Manufacturing: A Review", Organic Process Research & Development, 2021, vol. 25, pp. 16-42.
Laura Yvonne Pfund et al., "Towards Exhaustive and Automated High Throughput Screening for Crystalline Polymorphs", ACS Combinatorial Science, 2014 (18 pages).
Communication dated Jul. 21, 2026, issued in New Zealand Application No. 805567.
*Arthur* vs. *Glover/Rogers*, *Pharmalink International Ltd* vs. *Pharmazen Ltd*, "An appeal against a decision of the Commissioner of Patents", In the High Court of New Zealand Wellington Registry, CIV-2025-485-000053, 2025 NZHC 2657, hearing on Aug. 11-12, 2025, Judgment on Sep. 12, 2025, 31 pages.

* cited by examiner

[Figure 1]
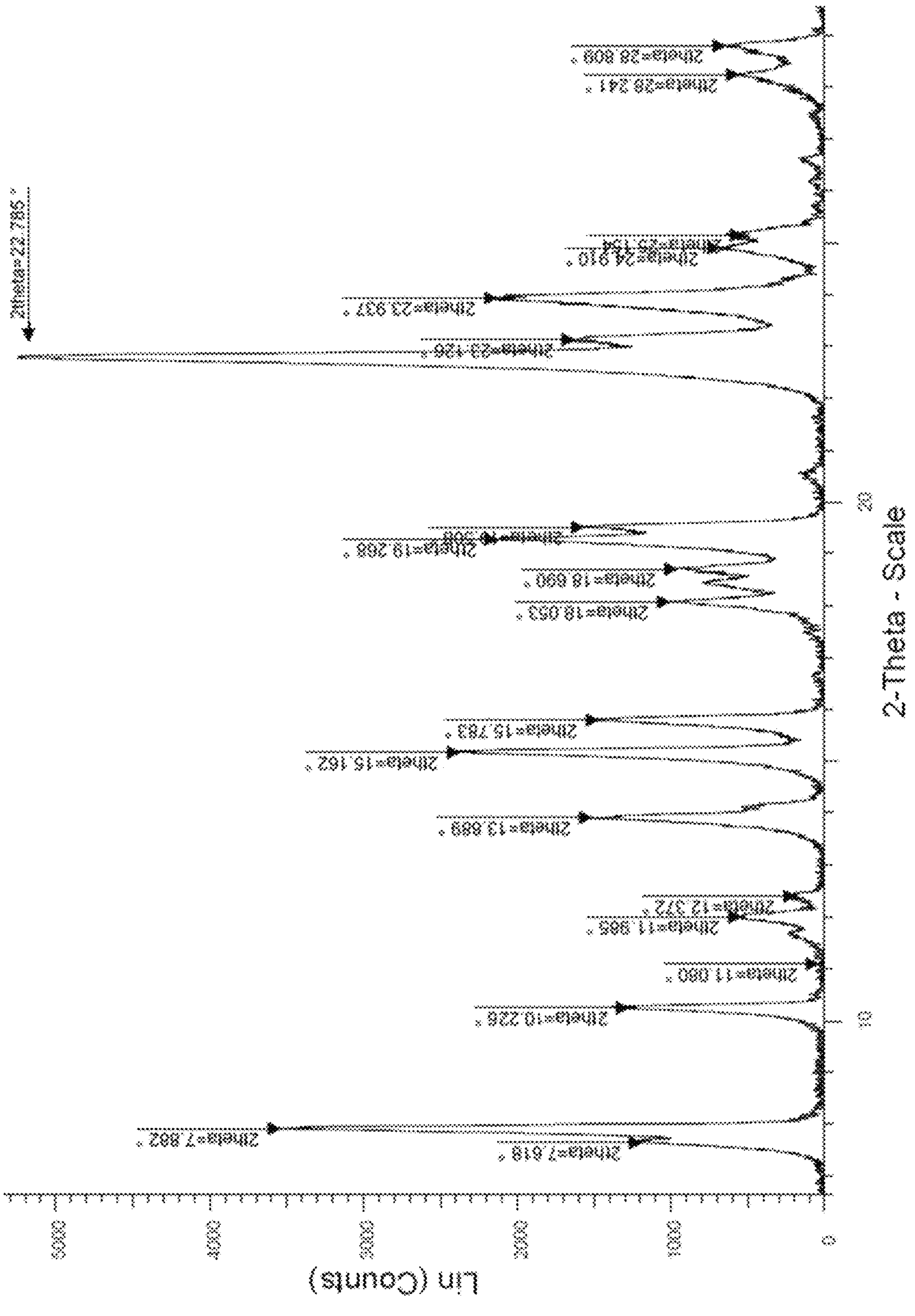

【Figure 2】
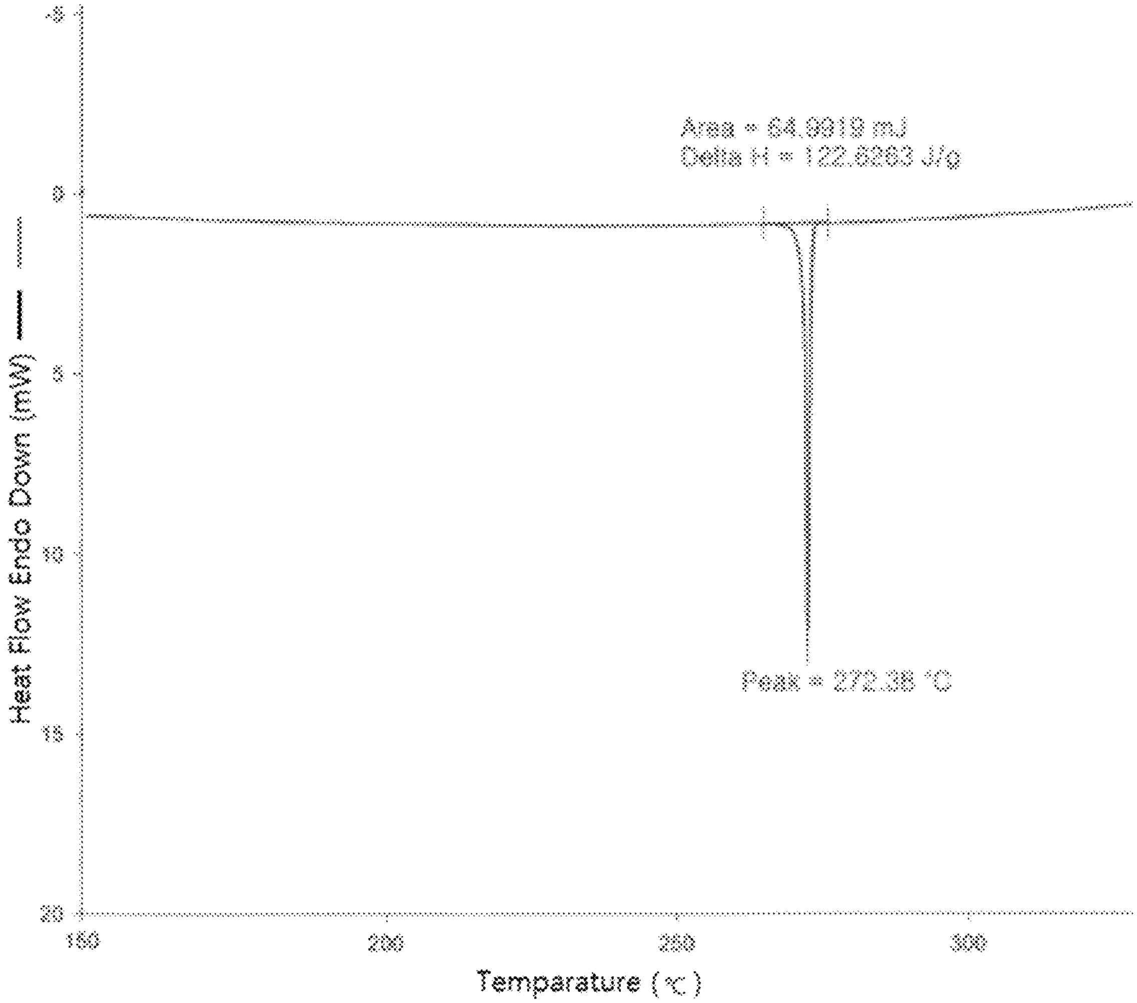

【Figure 3】
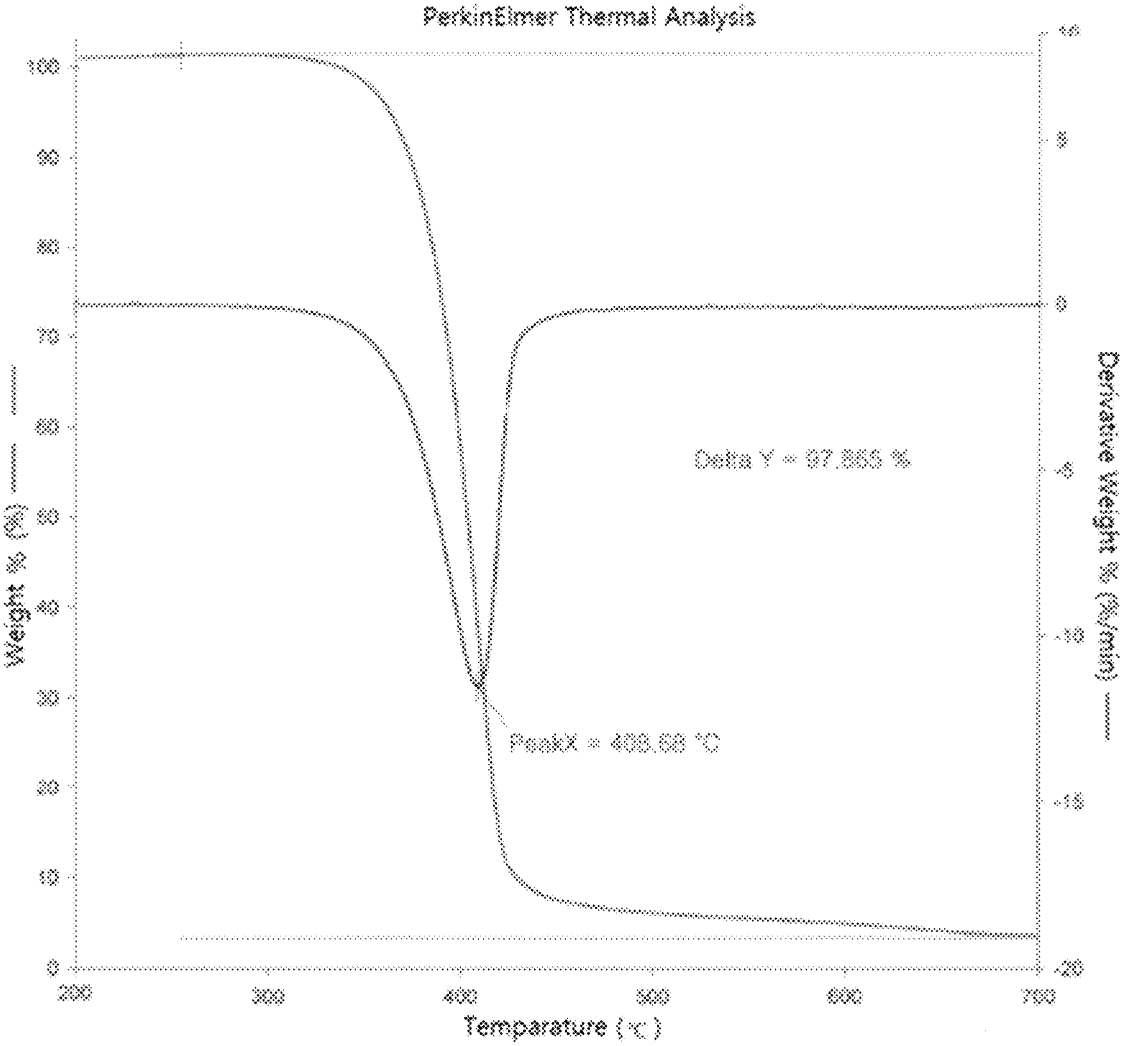

[Figure 4]
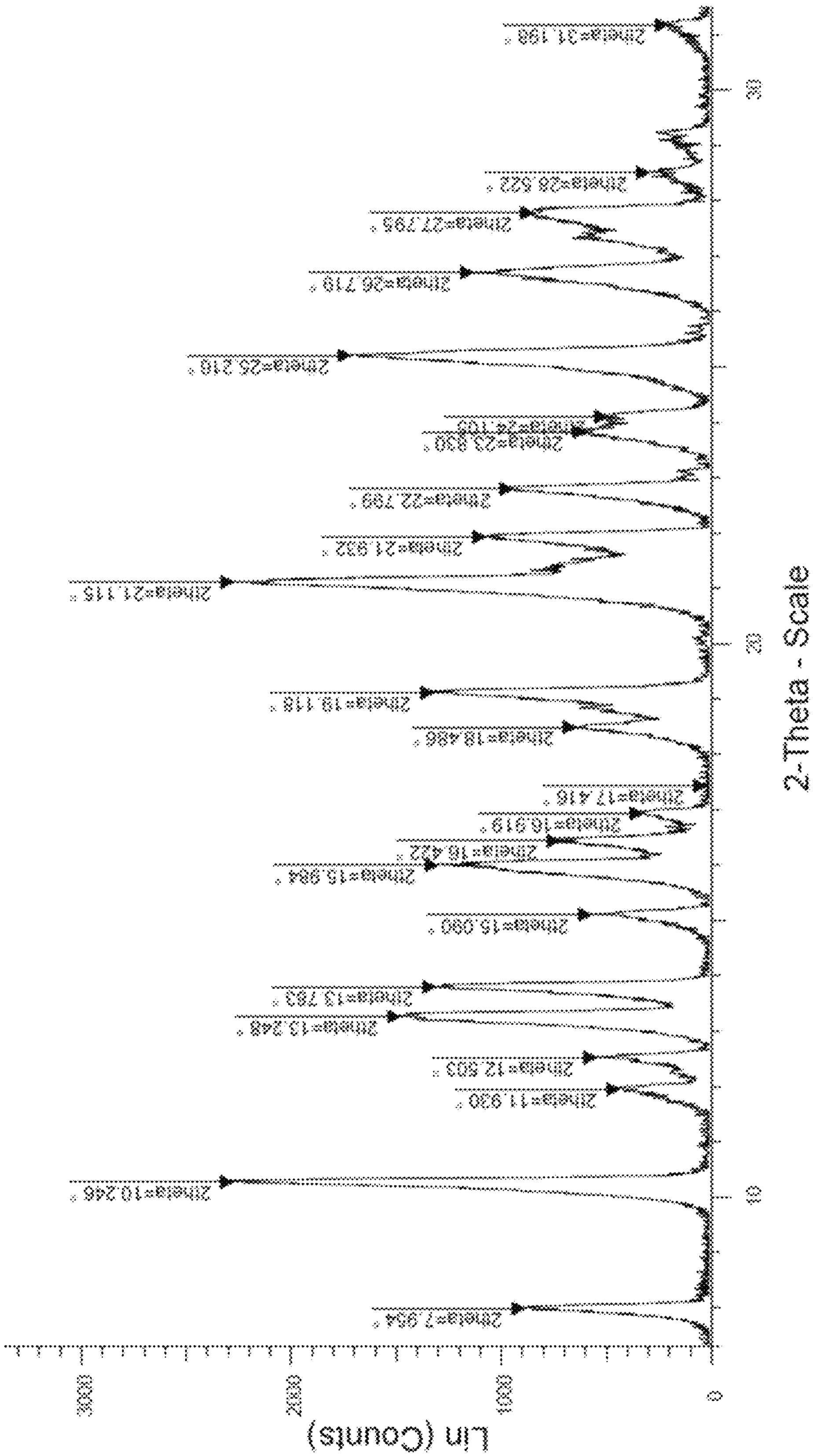

[Figure 5]
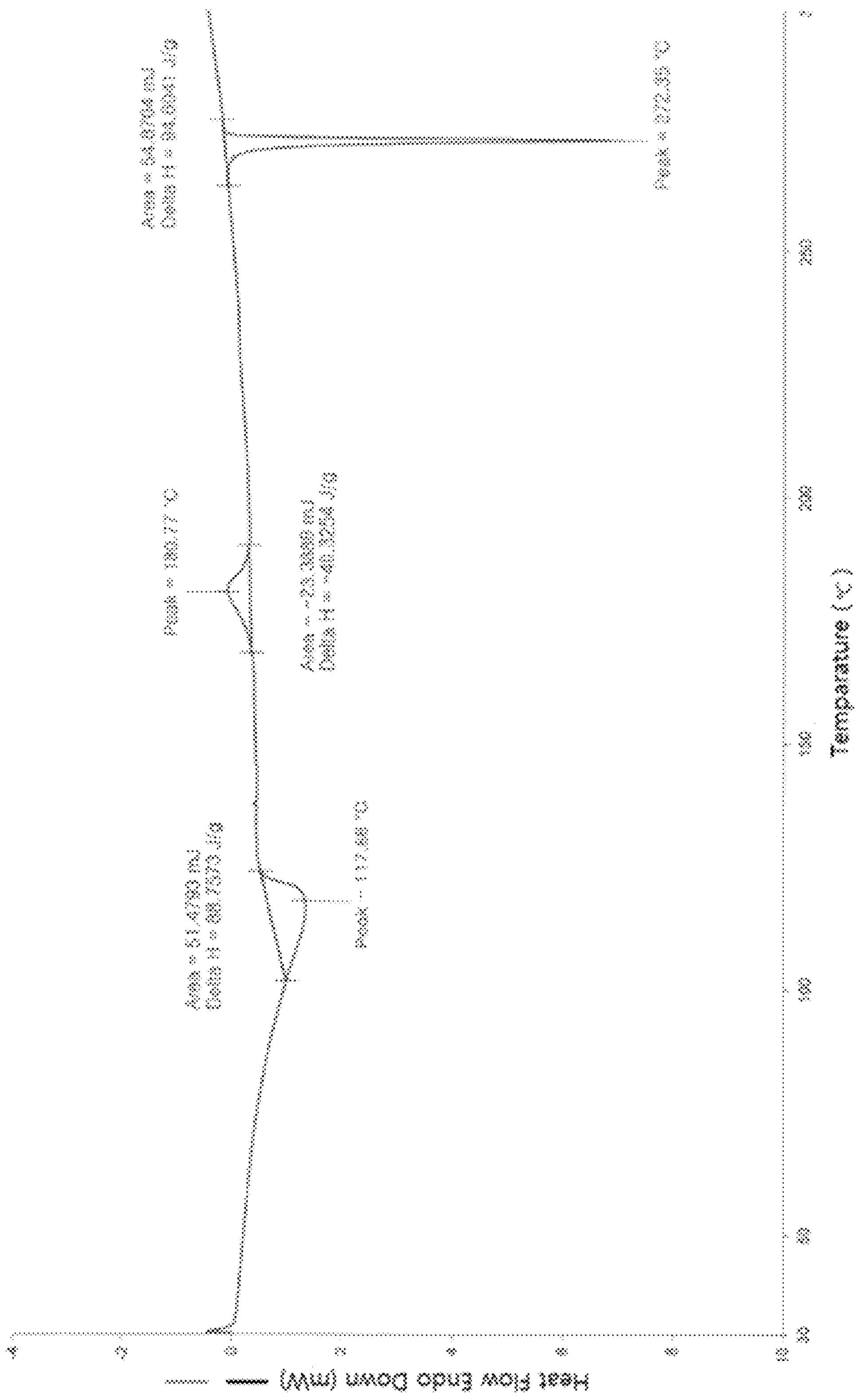

[Figure 6]
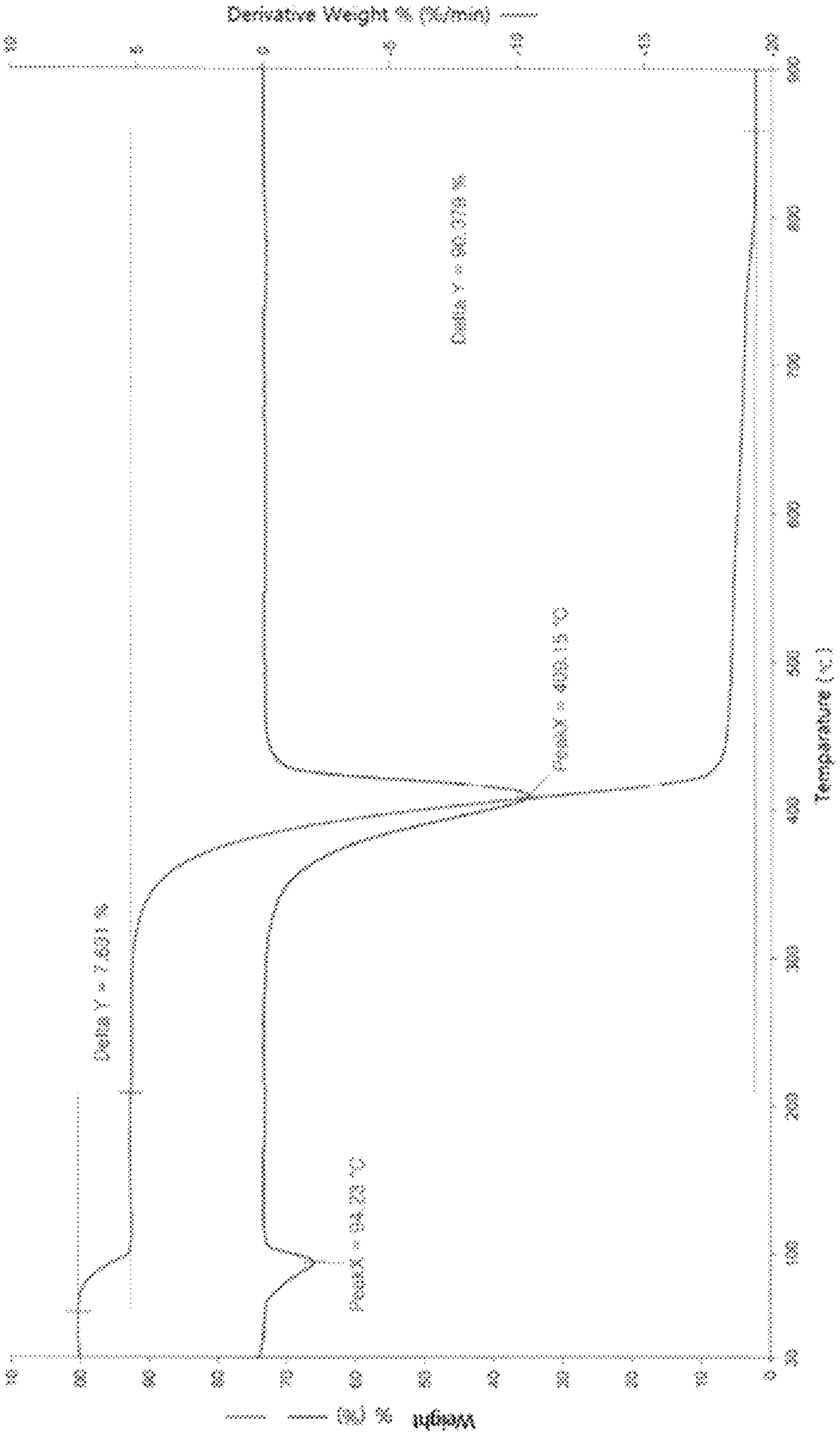

[Figure 7]
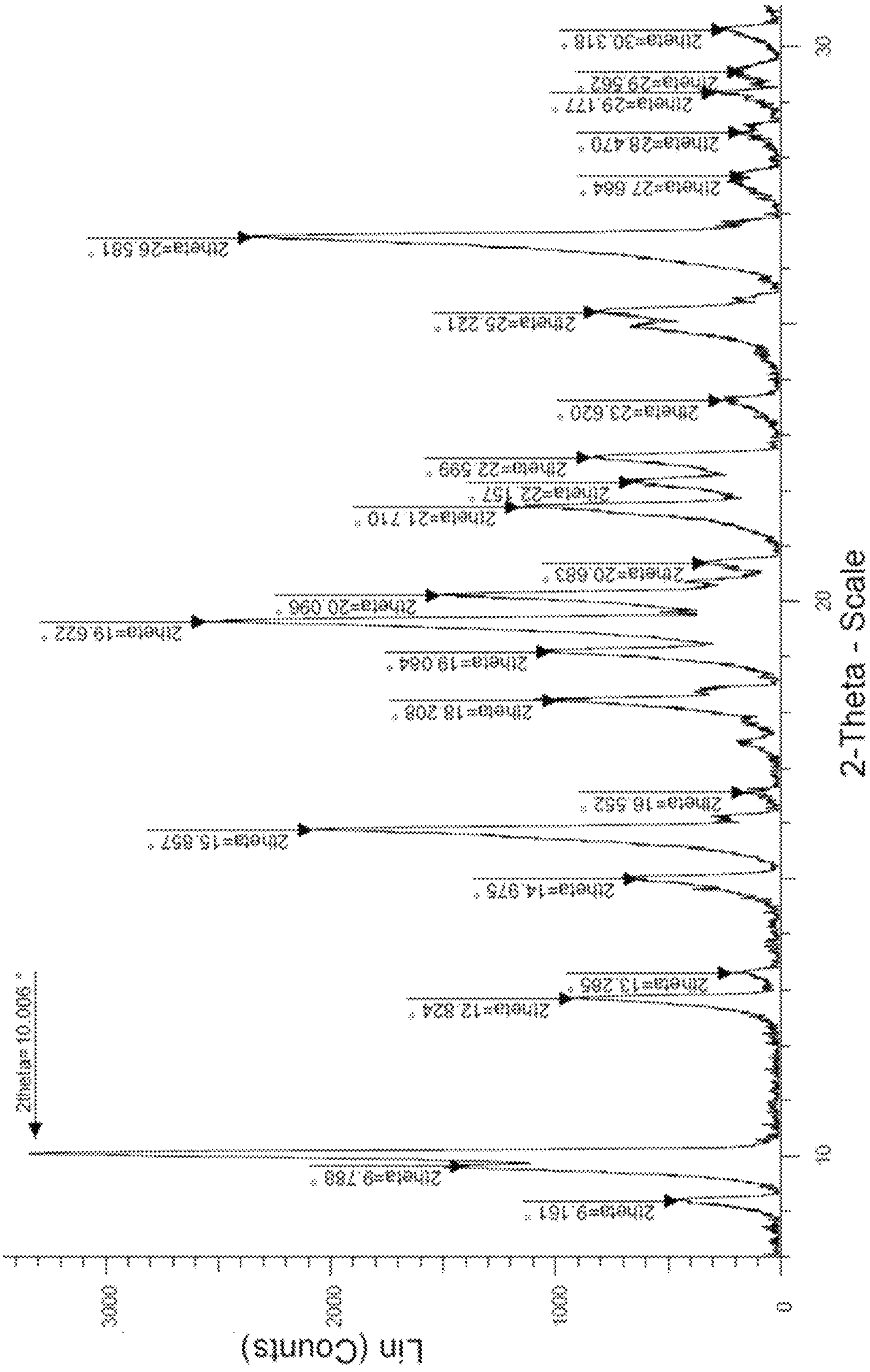

【Figure 8】
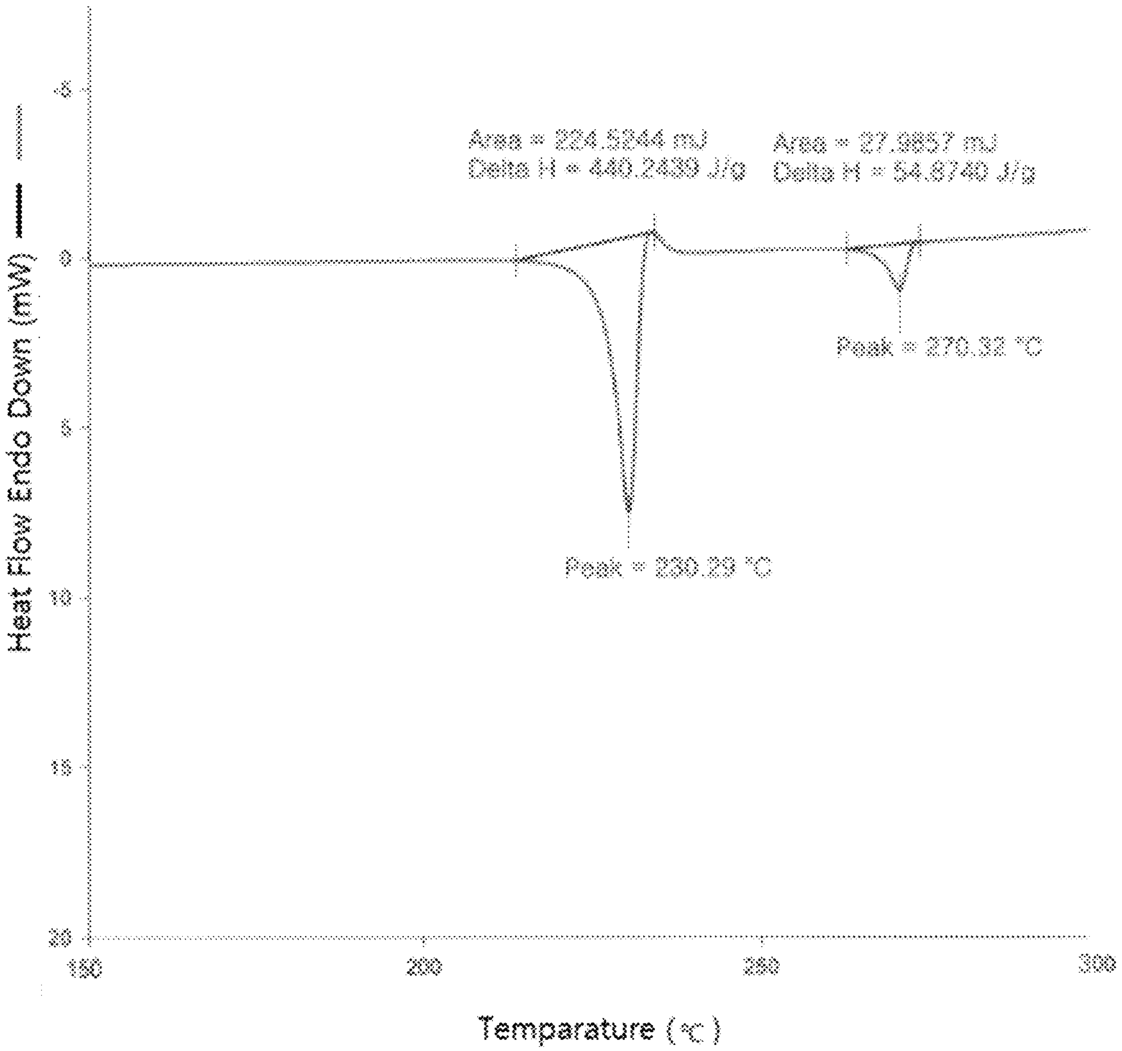

【Figure 9】
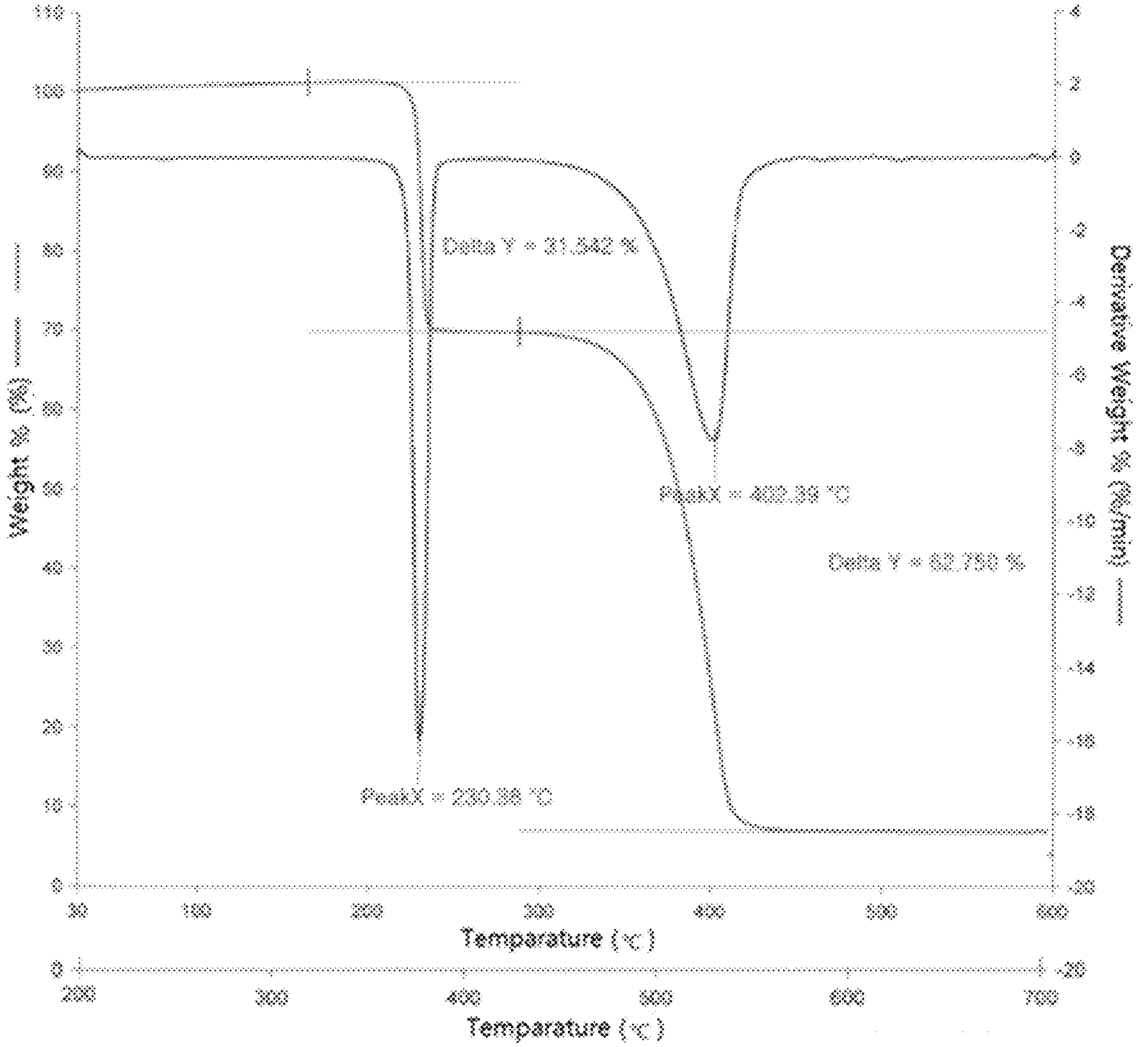

[Figure 10]
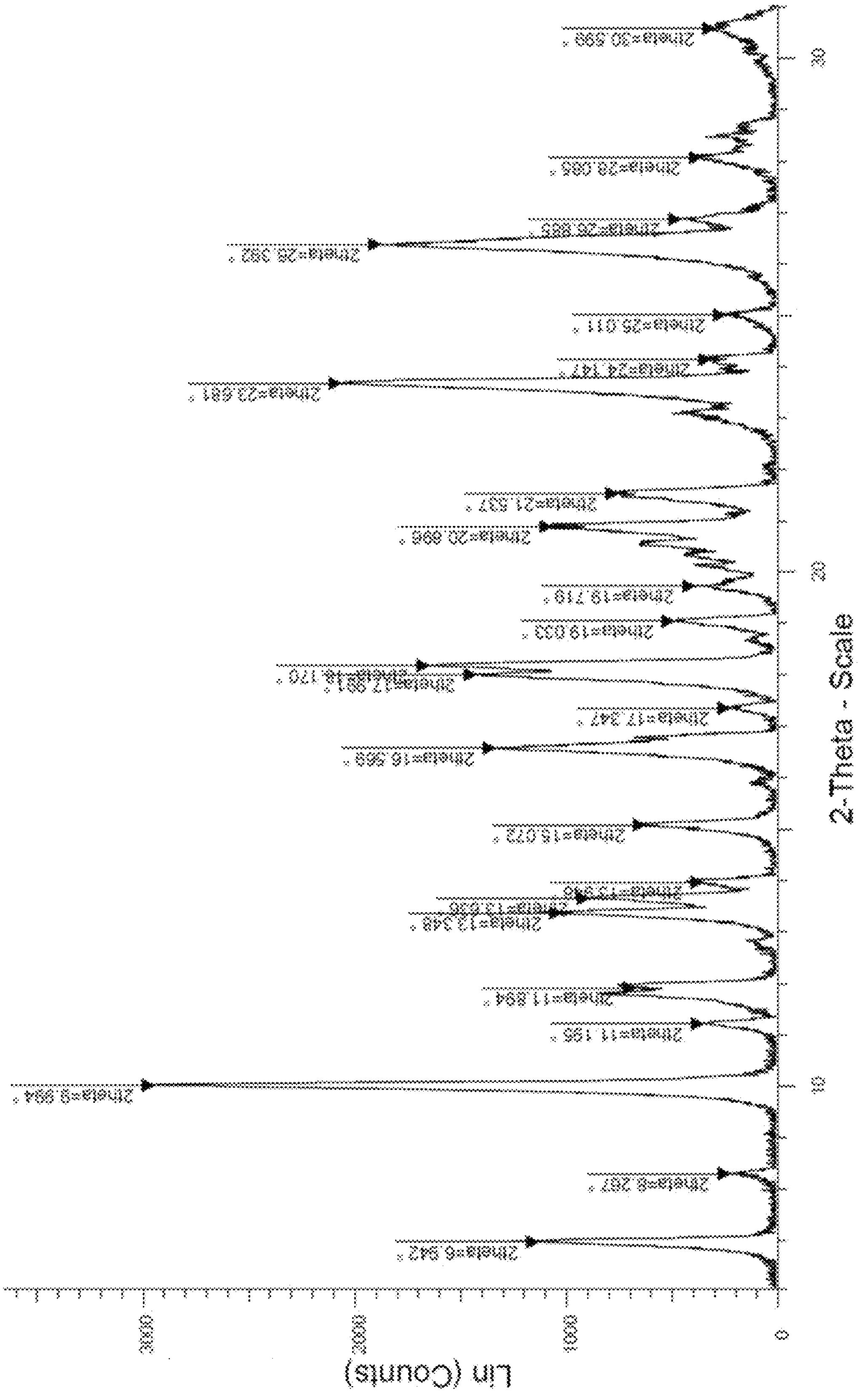

【Figure 11】
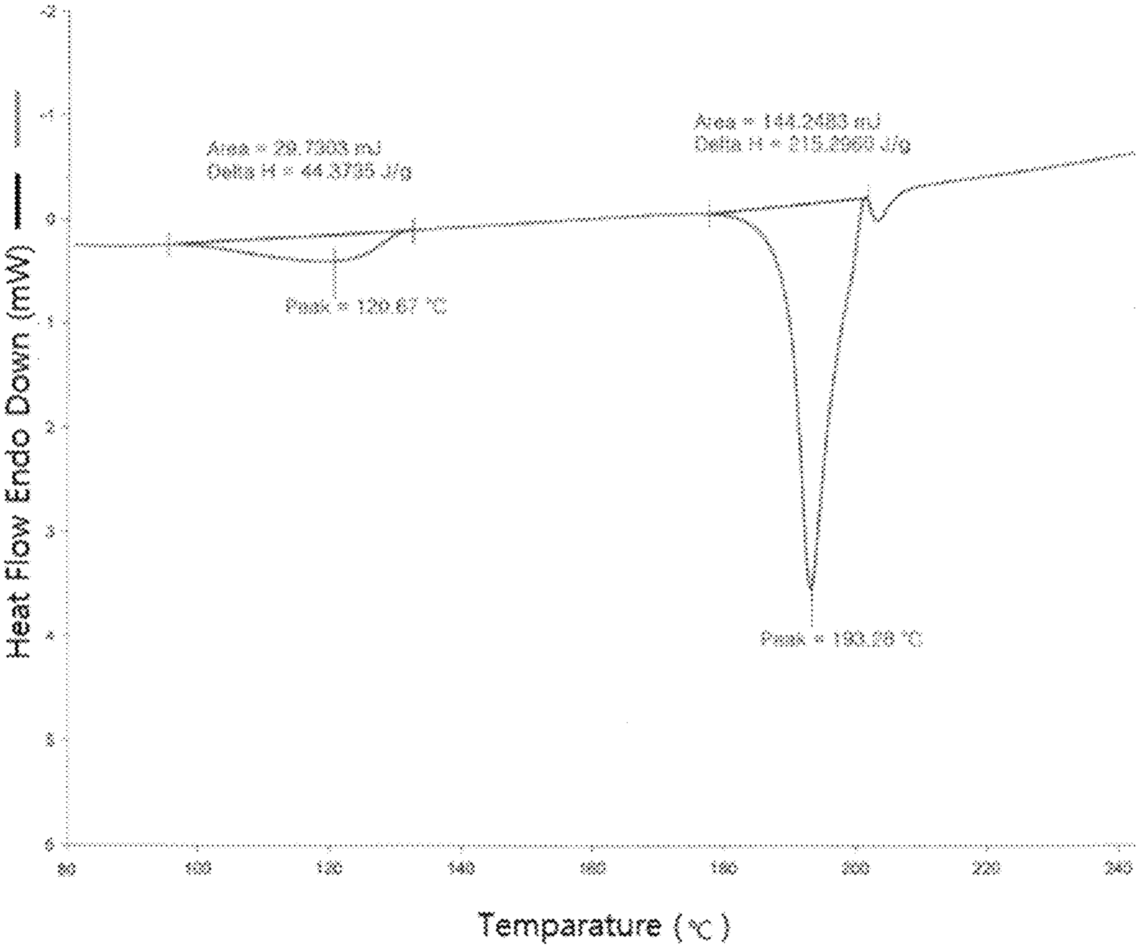

【Figure 12】
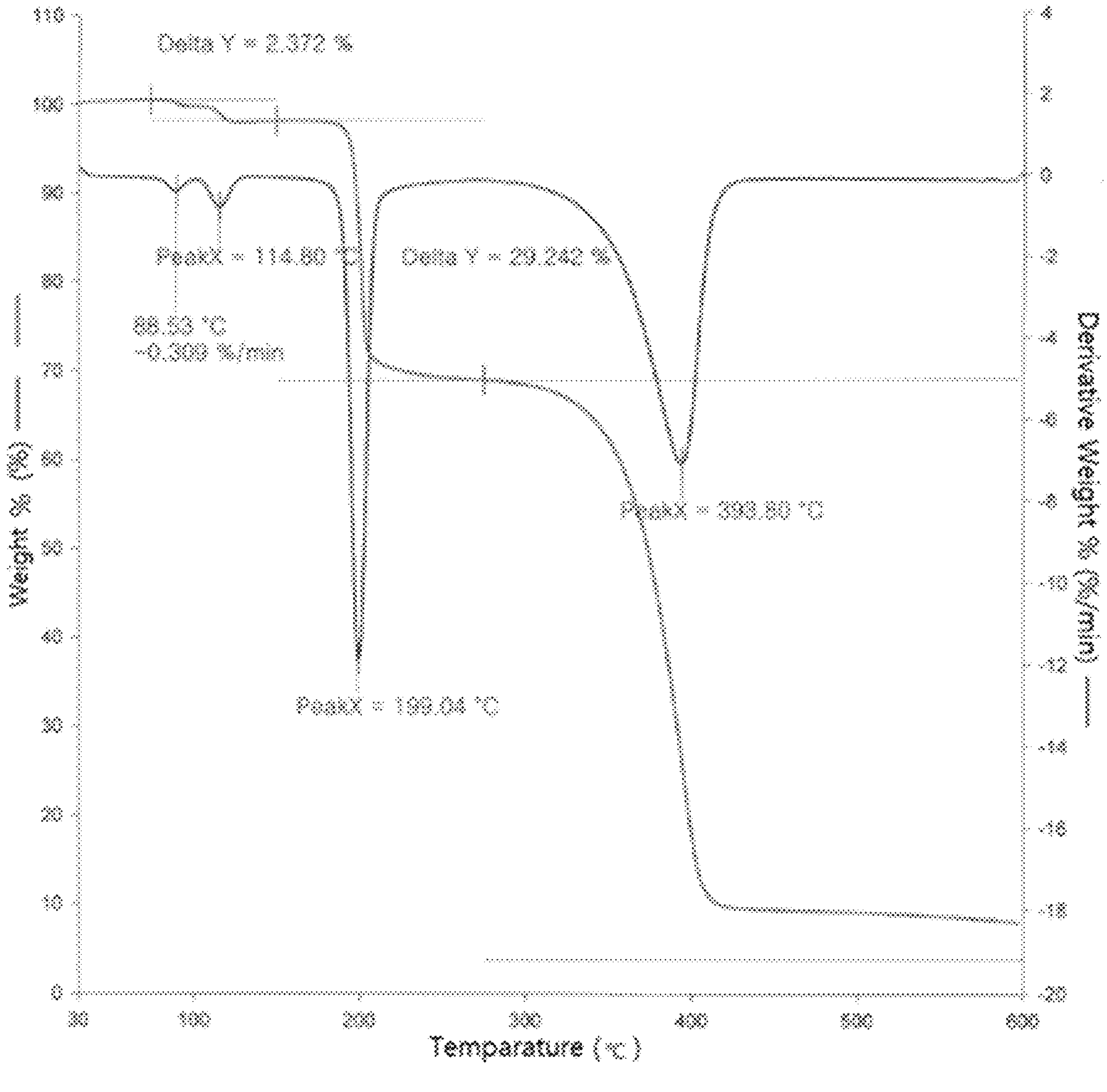

[Figure 13]
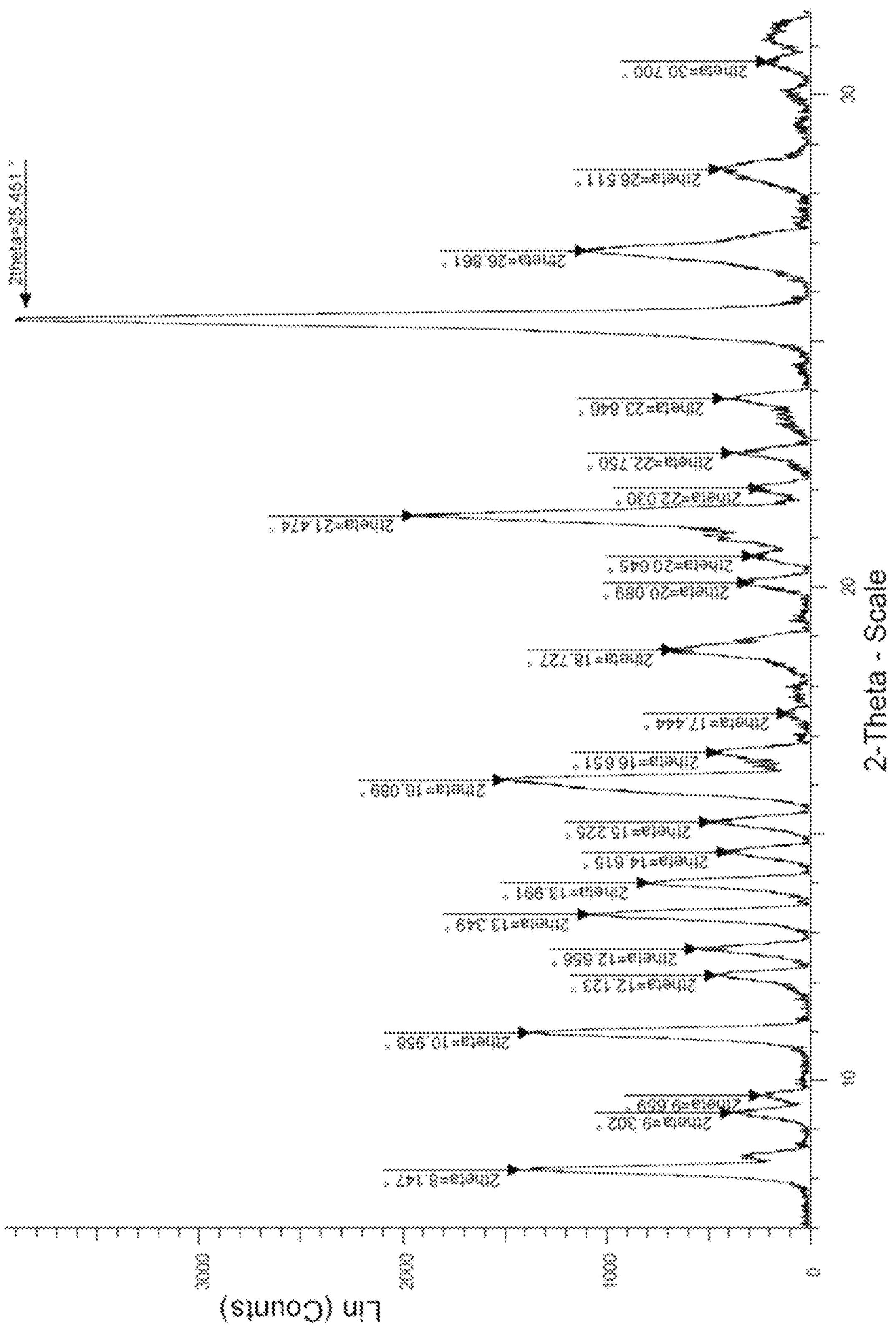

【Figure 14】
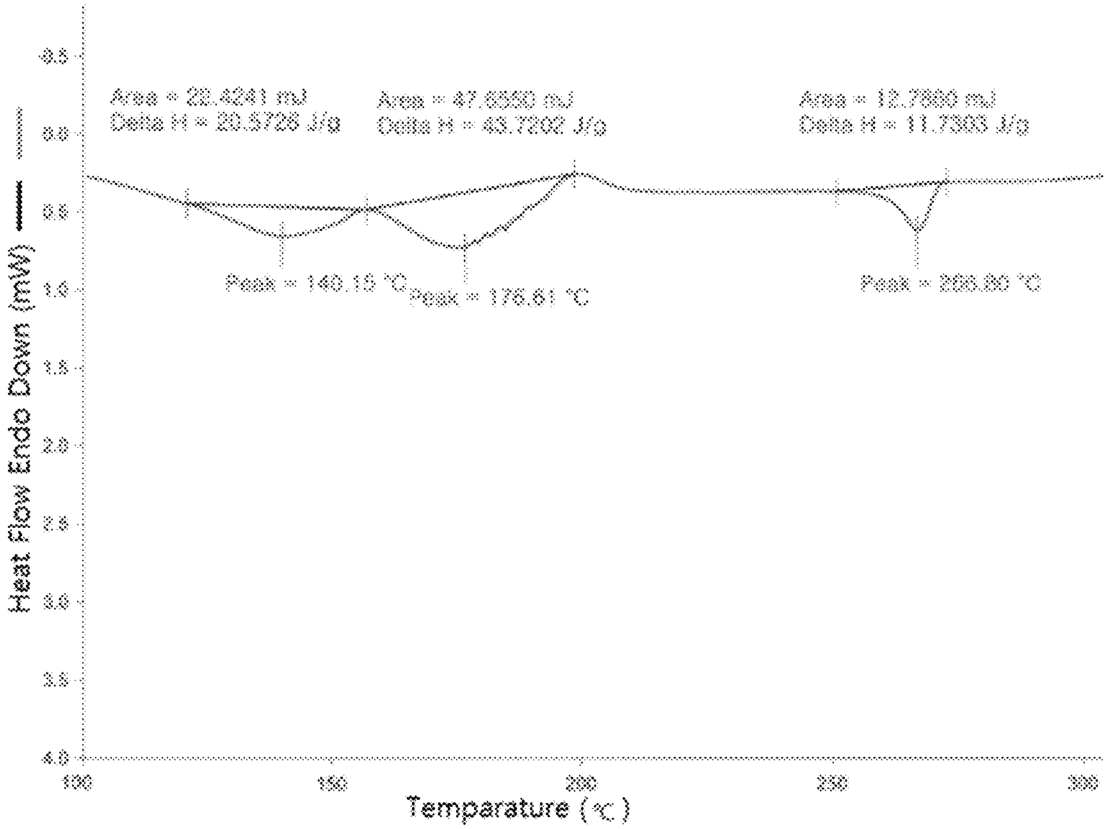

【Figure 15】
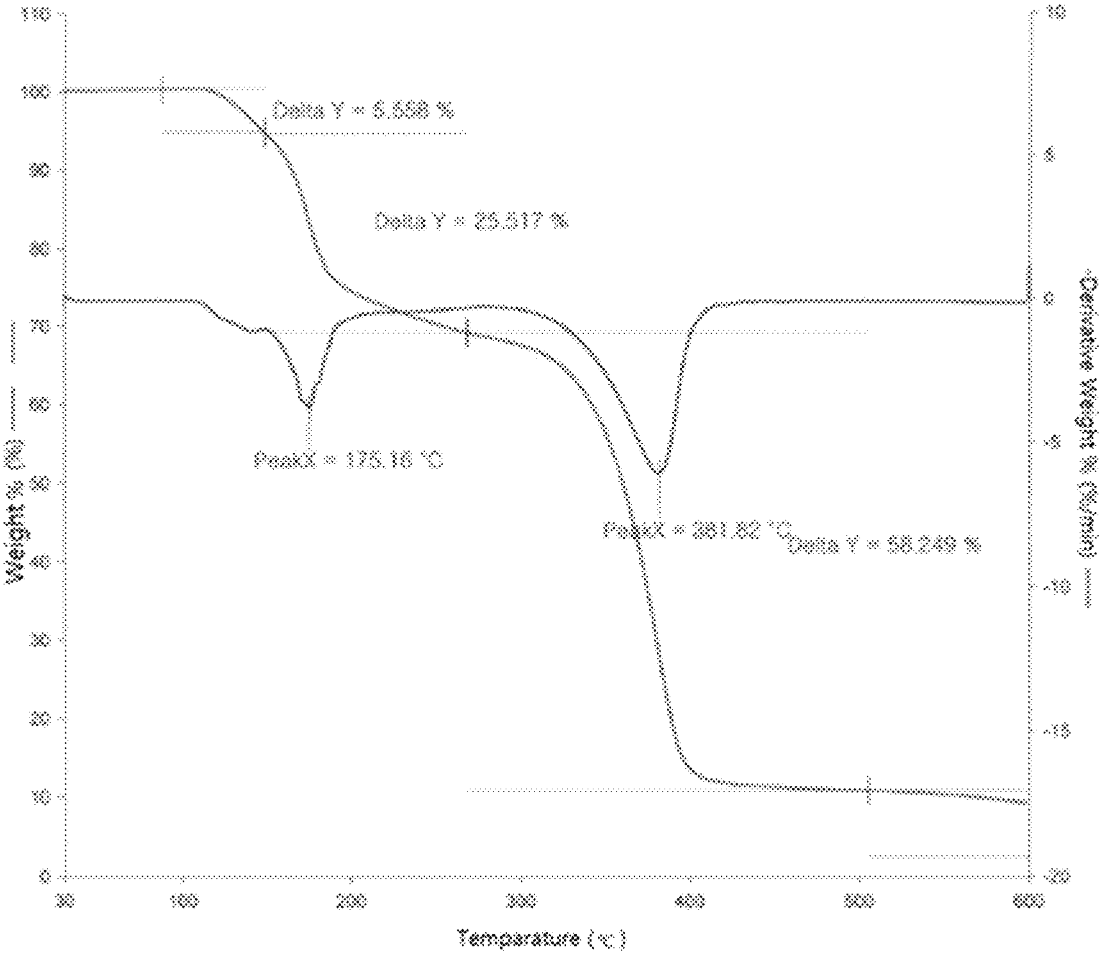

【Figure 16】
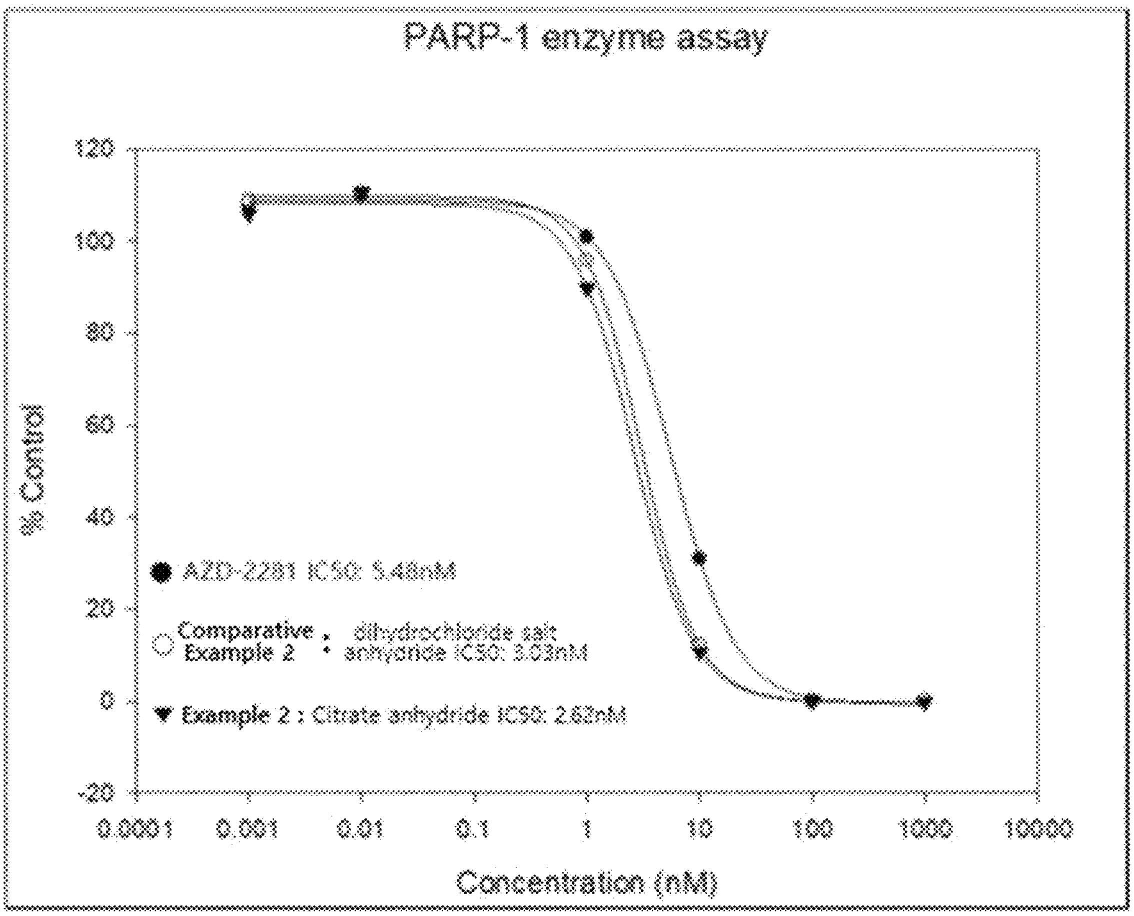

【Figure 17】
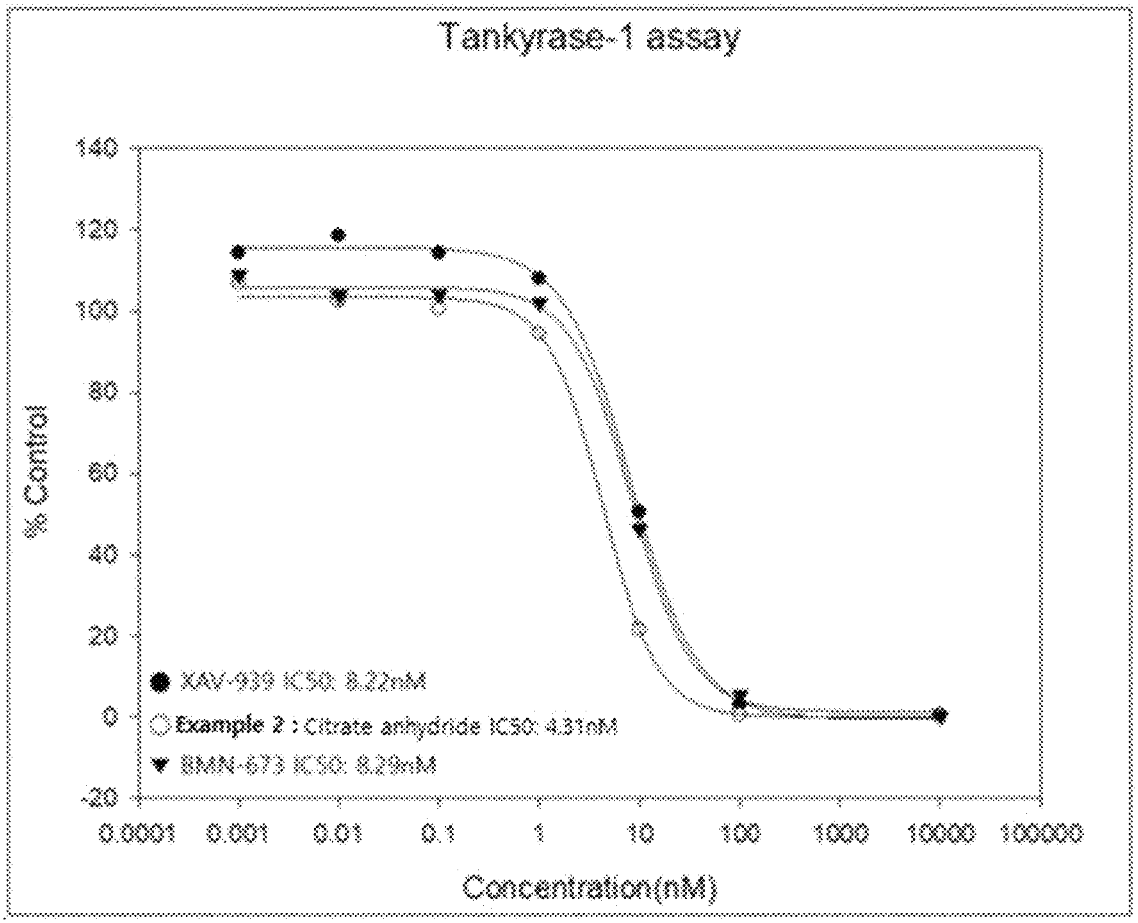

【Figure 18】
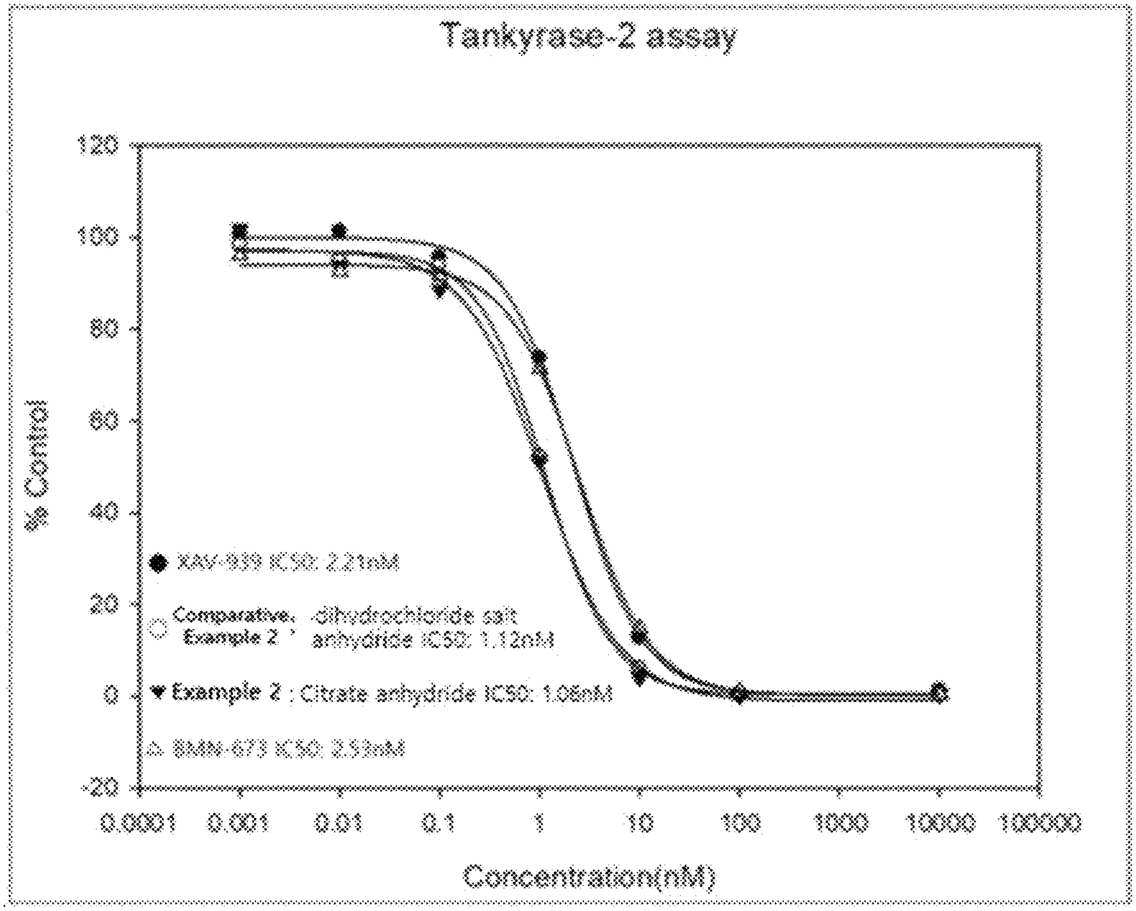

CRYSTALLINE FORM OF TRICYCLIC DERIVATIVE COMPOUND, METHOD FOR PREPARING SAME, AND PHARMACEUTICAL COMPOSITION COMPRISING SAME

This Application is a National Stage of International Application No. PCT/KR2022/007101 filed May 18, 2022, which claims the benefit of priority based on Korean Patent Application No. 10-2021-0064416 filed on May 18, 2021, the entire contents of which are incorporated herein as part of the present specification.

TECHNICAL FIELD

The present invention relates to a novel crystalline form of a salt of a tricyclic derivative compound having excellent poly(ADP-ribose) polymerase (PARP) and tankyrase inhibitory activity, a method for preparing the same, conversion of the crystalline form, and a pharmaceutical composition comprising the same.

BACKGROUND ART

Poly(ADP-ribose) polymerase (PARP) is composed of about 17 kinds of proteins, including PARP-1, PARP-2, PARP-3, PARP-4 (vPARP), PARP-5 (tankyrase-1, tankyrase-2), PARP-7, PARP-10, and the like (Curr Pharm Des., 13(9), 933-962, 2007). They all exhibit a certain level of homology in their catalytic domains, but have different functions in the cell (BioEssays., 26(8), 882-893, 2004).

The primary role of PARP-1 and PARP-2 is to facilitate DNA repair by ADP-ribosylation and to regulate the number of many DNA repair proteins. When DNA in cancer cells is damaged, PARP is activated to repair single-strand breaks in DNA, which may cause resistance in various types of cancer treatment. Thus, anticancer efficacy may be expected through PARP inhibitors, and in particular, it has been reported as useful for specific killing of tumors lacking DNA double-strand damage repair factors such as BRCA-1 and BRCA-2, and thus, it is being developed as a patient-specific anticancer drug for various cancer types such as breast cancer, ovarian cancer and prostate cancer with abnormal DNA double-strand damage repair factors (Nature, 434, 913-916, 2005; Cancer Biology & Therapy, 4, 934-936, 2005).

In addition, PARP inhibitors may be used for the treatment of various neurological and cardiovascular diseases, including ischemic brain injury, and are also useful for the treatment of inflammatory symptoms. Recently, the treatment possibility of PARP inhibitors has also been suggested for the treatment of diabetic neuropathy (Diabetes. 54 (12), 3435-3441, 2005).

On the one hand, tankyrase-1 and tankyrase-2, which are PARP-5, are known to be involved in Wnt/β-catenin signaling pathway, DNA repair process, and mitosis, which is highly related to the cell cycle [Biochimica et Biophysica Acta, 1846, 201-205, 2014]. In addition, they function as a positive regulator of telomere length. Therefore, inhibition of tankyrase-1 and tankyrase-2 may inhibit the Wnt/β-catenin signaling pathway, DNA repair process and telomere elongation, thereby exhibiting anticancer effects through a mechanism different from that of PARP-1 [Nature Reviews Drug Discovery, 11, 923-936, 2012].

International Publication No. WO 2016/200101 discloses various tricyclic derivative compounds, which are inhibitors of PARP-1 and tankyrases, that may be used for the treatment of diseases caused by the activity of poly(ADP-ribose) polymerase (PARP). These compounds are prepared in the form of free base or mono- to tri-hydrochloride salts, and most of them are in the form of hydrochloride salts. The present inventors have confirmed that the compounds prepared in International Publication No. WO 2016/200101 have water solubility so low that they are difficult to use as pharmaceuticals, and have to go through several steps to prepare the compounds, and thus, they are not preferable for commercial use. Accordingly, the present invention has been completed by developing a novel crystalline form of a salt having water solubility applicable to pharmaceuticals and ensuring stability such as photostability, and a novel method for the same that may be used for commercial use. The preparation method of the present invention may prepare a high-purity compound in a stable crystalline form without an additional purification process after completion of the reaction, and thus, it provides a commercially very useful method while enabling mass production.

DISCLOSURE

Technical Problem

It is an object of the present invention to provide a novel crystalline form of a salt of a tricyclic derivative compound having excellent PARP-1, tankyrase-1 or tankyrase-2 inhibitory activity, and an effective method for preparing the same.

From the above, its object is to solve the problems of the prior art, especially low water solubility that is not applicable to pharmaceuticals, and to improve the inefficiency of having to go through several steps to increase purity, and at the same time reduce related substances that are difficult to separate/remove after generation.

It is another object of the present invention to provide a pharmaceutical composition for preventing or treating various diseases caused by the activity of PARP-1, tankyrase-1 or tankyrase-2, comprising a crystalline form of a citrate of the tricyclic derivative compound as an active ingredient.

Technical Solution

Crystalline Form of Citrate of a Tricyclic Derivative Compound

The present invention provides a crystalline form of a citrate of a tricyclic derivative compound represented by Formula 1 below:

[Formula 1]

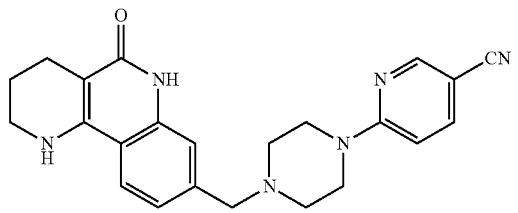

The crystalline form of the citrate of the tricyclic derivative compound may be an anhydride.

The crystalline form of the anhydride may contain about 1% by weight or less, preferably 0.5% by weight or less of water.

The crystalline form of the anhydride is characterized by comprising 2θ(±0.2° values of 10.01°, 15.86°, 19.62°, and 26.58° in the powder XRD pattern.

In addition, the crystalline form of the anhydride may further comprise 2θ(±0.2° values of 9.79°, 20.10°, and 27.71° in the powder XRD pattern.

In addition, the crystalline form of the anhydride substantially shows an XRD pattern as shown in FIG. 7.

The crystalline form of the citrate of the tricyclic derivative compound may be a monohydrate.

The crystalline form of the monohydrate may contain water in the range of about 2.0 to 4.5% by weight, preferably about 3% by weight of water.

The crystalline form of the monohydrate is characterized by comprising 2θ(±0.2°) values of 6.94°, 9.99°, 16.57°, 18.17°, 23.68°, and 26.39° in the powder XRD pattern.

In addition, the crystalline form of the monohydrate may further comprise 2θ(±0.2°) values of 11.89°, 13.35°, 15.07U and 20.90° in the powder XRD pattern.

In addition, the crystalline form of the citrate monohydrate substantially shows an XRD pattern as shown in FIG. 10.

The citrate of the tricyclic derivative compound may be a dihydrate.

The crystalline form of the dihydrate may contain water in the range of about 5.0 to 7.5% by weight, preferably about 5.7% by weight of water. The crystalline form of the dihydride is characterized by comprising 2θ(±0.2°) values of 8.15°, 10.96°, 16.09°, 21.47°, 25.45° and 26.86° in the powder XRD pattern.

In addition, the crystalline form of the dihydrate may further comprise 2θ(±0.2°) values of 13.35°, 18.73° and 28.51° in the powder XRD pattern.

In addition, the crystalline form of the citrate dihydrate substantially shows an XRD pattern as shown in FIG. 13.

The crystalline form of the citrate of the tricyclic derivative compound of the present invention may be characterized in that the purity is maintained at 95% or more, preferably 96% or more after irradiation with UV light having a light intensity of 35 W to a total irradiation amount of 200 watts under conditions of 25° C. and 60% humidity in a photostability chamber.

In addition, it may be characterized in that the purity is maintained at 95% or more, preferably 96% or more after irradiation with visible light having a light intensity of 35 k Lux to a total irradiation amount of 1200 k lux under conditions of 25° C. and 60% humidity.

That is, the crystalline form of the citrate of the tricyclic derivative compound of the present invention provides very excellent photostability compared to conventional hydrochloric acid salts and the like.

The crystalline form of the citrate of the tricyclic derivative compound may be characterized in that the peak area (%) of related substances is less than 0.05% at RT 43 min to 45 min in HPLC analysis, and more preferably, peaks of related substances are not observed (non-existent) at RT 43 min to 45 min.

In addition, the crystalline form of the citrate of the tricyclic derivative compound may be characterized in that the peak area (%) of related substances is less than 0.15%, preferably less than 0.1%, more preferably less than 0.05% and still more preferably less than 0.015%, and most preferably, peaks of related substances are not observed (non-existent) at RT 48 min to 50 min in HPLC analysis.

In addition, the crystalline form of the citrate of the tricyclic derivative compound may be characterized in that peaks of related substances are not observed (non-existent) at RT 43 min to 45 min and RT 48 min to 50 min in HPLC analysis.

The related substances observed at RT 48 min to 50 min has the following chemical structure:

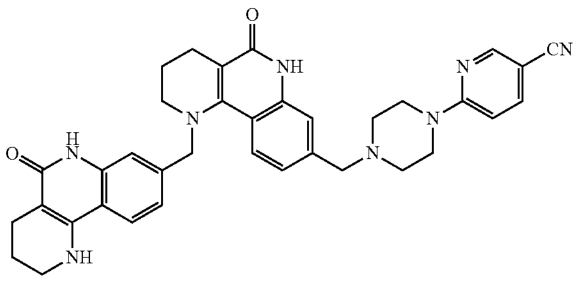 [SMILES: N#Cc1ccc(N2CCN(Cc3ccc4c5c(c(=O)[nH]c4c3)CCCN5Cc3ccc4c5c(c(=O)[nH]c4c3)CCCN5)CC2)nc1]

Since the related substances are difficult to separate and remove after generation and are harmful to the human body, safety confirmation tests must be additionally conducted if they are generated in excess of the standard. Thus, it is very important to reduce the related substances in the preparation process.

The crystalline form of the citrate of the tricyclic derivative compound may be characterized by having a purity of 99.6% or more.

In addition, it may be characterized by having a purity of 99.6% or more when stored for 3 months under long-term storage conditions (stored at a temperature of 25±2° C. and humidity of 60±5%). In addition, it may be characterized by having a purity of 99.5% or more, preferably 99.55% or more when stored for 6 months. In addition, it may be characterized by having a purity of 99.7% or more when stored for 12 months. In addition, it may be characterized by having a purity of 99.7% or more when stored for 24 months. In addition, it may be characterized by having a purity of 99.7% or more when stored for 36 months.

In addition, it may be characterized in that the purity does not decrease compared to the initial purity when stored for 9 months or more under long-term storage conditions (stored at a temperature of 25±2° C. and humidity of 60±5%).

In addition, it may be characterized by having a purity of 99.6% or more when stored for 3 months and a purity of 99.5% or more when stored for 6 months under accelerated storage conditions (stored at a temperature of 40±2° C. and humidity of 75±5%).

The crystalline form of the citrate of the tricyclic derivative compound may be characterized in that the peak area (%) of related substances is 0.30% or less, more preferably 0.29% or less in HPLC analysis after 3 months storage under long-term storage conditions (stored at a temperature of 25±2° C. and humidity of 60±5%). In addition, it may be characterized in that the peak area (%) of related substances is 0.32% or less, more preferably 0.30% or less in HPLC analysis after 6 months storage. In addition, it may be characterized in that the peak area (%) of related substances is 0.32% or less, preferably 0.30% or less in HPLC analysis after 12 months storage. In addition, it may be characterized in that the peak area (%) of related substances is 0.35% or less in HPLC analysis after 24 months storage. In addition, it may be characterized in that the peak area (%) of related substances is 0.32% or less in HPLC analysis after 36 months storage.

The crystalline form of the citrate of the tricyclic derivative compound may be characterized in that the peak area (%) of related substances is 0.35% or less, more preferably 0.25% or less in HPLC analysis after 3 months storage under accelerated storage conditions (stored at a temperature of 40±2° C. and humidity of 75±5%). In addition, it may be characterized in that the peak area (%) of related substances is 0.33% or less, more preferably 0.30% or less in HPLC analysis after 6 months storage.

Crystalline Form of a Tricyclic Derivative Compound

In addition, the present invention provides a crystalline form of a tricyclic derivative compound represented by Formula 1 below:

[Formula 1]

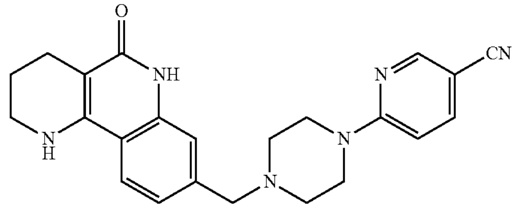

The tricyclic derivative compound (free base) of Formula 1 is an active ingredient that exhibits the efficacy of PARP and tankyrase inhibitors in vivo, and is also very usefully used as an intermediate for the preparation of a crystalline form of citrate, which is an acid addition salt thereof.

The crystalline form of the tricyclic derivative compound may be an anhydride.

The crystalline form of the anhydride is characterized by containing about 1% by weight or less, preferably 0.5% by weight or less of water.

The crystalline form of the tricyclic derivative compound is characterized by comprising 2θ(±0.2°) values of 7.88°, 10.23°, 15.16°, 19.27°, 22.79° and 23.94° in the powder XRD pattern.

In addition, the crystalline form of the tricyclic derivative compound may further comprise 2θ(±0.2°) values of 13.89°, 15.78°, 18.05° and 19.51° in the powder XRD pattern.

In addition, the crystalline form of the tricyclic derivative compound substantially shows an XRD pattern as shown in FIG. 1.

The crystalline form of the tricyclic derivative compound may be a dihydrate.

The crystalline form of the dihydrate may be characterized by containing water in the range of about 7.0 to 9.5% by weight, preferably about 8.3% by weight of water.

The crystalline form of the dihydride is characterized by comprising 2θ(±0.2° values of 7.95°, 10.25°, 13.25°, 13.78°, 21.12°, and 25.22° in the powder XRD pattern.

In addition, the crystalline form of the dihydrate may further comprise 2θ(±0.2° values of 11.93°, 12.50°, 15.98°, 19.12°, 22.80° and 26.72° in the powder XRD pattern.

In addition, the crystalline form of the dihydrate substantially shows an XRD pattern as shown in FIG. 4.

Method for Preparing a Crystalline Form of Citrate of a Tricyclic Derivative Compound <1$^{st}$ Method>

The present invention provides a method for preparing the crystalline form of the citrate of the tricyclic derivative compound, as shown in Scheme 1-1 below. The preparation method of the present invention has the characteristics of providing excellent yield and purity and remarkably improving preparation efficiency by simplifying the preparation process.

The crystalline form of the citrate of the tricyclic derivative compound represented by Formula 1 of the present invention may be prepared by comprising the steps of:

(a) obtaining a crystalline compound of Formula 1 by reacting a compound of Formula 2 with a compound of Formula 3 in Scheme 1-1 below and then performing a crystallization process; and (b) reacting the crystalline compound of Formula 1 above with citric acid at 50 to 80° C. in one or more solvents selected from the group consisting of an organic solvent and water:

[Scheme 1-1]

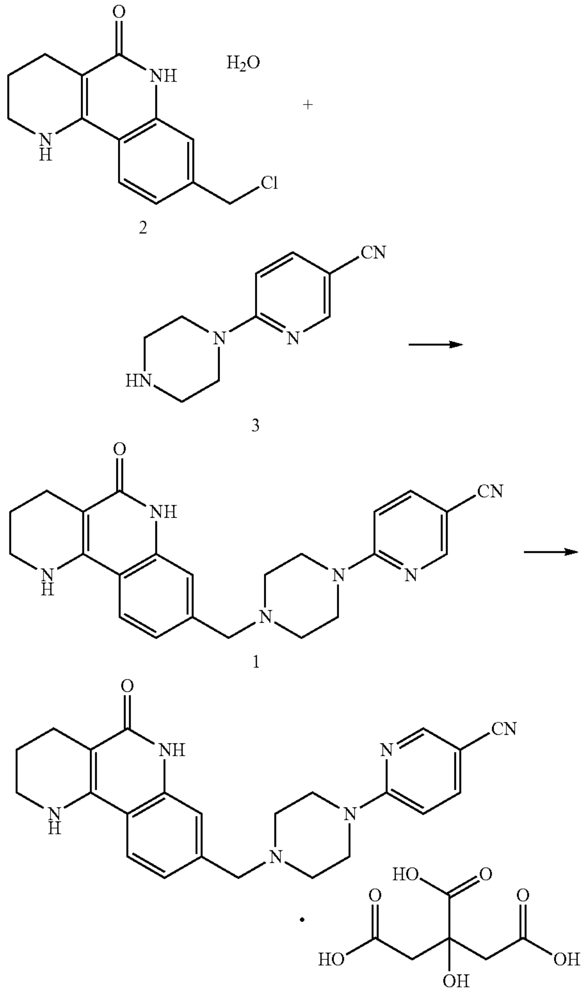

2

3

1

Hereinafter, the preparation method will be described step by step in detail.

<Step (a)>

The reaction in step (a) above may be performed in the presence of an organic amine such as pyridine, triethylamine and diethylisopropylamine, or a base such as potassium carbonate.

The reaction temperature is not particularly limited, but may be generally carried out at cold temperature to elevated temperature, preferably at room temperature to elevated temperature.

In particular, as the reaction solvent in step (a) above, at least one selected from N, N-dimethylformamide (DMF), dimethylacetamide (DMAC), N-methylpiperidone (NMP), dimethylsulfoxide (DMSO), and the like may be used, and when these solvents are used, compared to the case of using conventional organic solvents, the reaction time is dramatically shortened (reaction time reduced from 24 hours to 6 hours), stirring under reflux is unnecessary, and additional processes such as additional recrystallization and chromatography are unnecessary due to the reduction of related substances, and thus, the effect of greatly simplifying the process is provided.

In the crystallization process of step (a), at least one selected from methanol, ethanol, isopropanol, butanol, acetone, acetonitrile, ethyl acetate, tetrahydrofuran and water may be used as the crystallization solvent. Purified water or distilled water may be used as water.

In particular, when water is used as the crystallization solvent, high-yield, high-purity crystals may be prepared without additional processes such as recrystallization, and the process may be greatly simplified, and thus, it is suitable for mass synthesis processes.

Furthermore, in step (a) above, when dimethylformamide (DMF) is used as the reaction solvent and water is used as the crystallization solvent, a better effect is provided. That is, high-yield, high-purity crystals may be prepared without additional processes such as recrystallization, and the process may be greatly simplified, and thus, it is suitable for mass synthesis processes.

The reaction in step (a) above may be carried out at 35 to 55° C., and a filtration process may be further performed after the crystallization process. In particular, step (a) of the present invention has a characteristic of providing excellent purity to the extent that recrystallization and the like are unnecessary.

<Step (b)>

The citrate of the tricyclic derivative compound prepared by the preparation method may be an anhydride or a hydrate, and the hydrate may be a monohydrate or dihydrate.

Among the solvents in step (b) above, at least one selected from methanol, ethanol, acetone, isopropanol, acetonitrile, butanol, propanol and tetrahydrofuran may be used as the organic solvent.

Purified water or distilled water may be used as water throughout the present invention.

The citrate of the tricyclic derivative compound prepared by the preparation method may be prepared in crystalline form, and when it is a crystalline form of citric acid anhydride, an organic solvent among the solvents described above may be used as the solvent in step (b) above, and a mixed solvent of methanol and ethanol may be preferably used. In this case, methanol and ethanol in the mixed solvent may be mixed and used in a volume ratio of 1:9 to 9:1, and preferably used in a volume ratio of 4:9 to 2:7.

In addition, when the citrate of the tricyclic derivative compound is a monohydrate, the organic solvent and water described above may be mixed and used in a volume ratio of 1:9 to 9:1 as the solvent in step (b) above, and a mixed solvent of methanol and water may be preferably used. In this case, methanol and water in the mixed solvent may be used in a volume ratio of 3:7 to 7:3.

In addition, when the citrate of the tricyclic derivative compound is a dihydrate, the organic solvent and water described above may be mixed and used in a volume ratio of 2:8 to 0:10 as the solvent in step (b) above, and water may be preferably used.

After the reaction in step (b) above is completed, a filtration process may be further performed on the reaction product. In this case, a crystalline compound may be obtained with excellent purity and yield by filtration and drying after completion of the reaction even without additional processes such as additional recrystallization and chromatography.

<2$^{nd}$ Method>

The present invention provides a method for preparing the crystalline form of the citrate of the tricyclic derivative compound, as shown in following Scheme 1-2. The preparation method of the present invention has the characteristics of providing excellent yield and purity and remarkably improving preparation efficiency by simplifying the preparation process.

The crystalline form of the citrate of the tricyclic derivative compound represented by Formula 1 above of the present invention may be prepared by comprising the steps of:

(1) obtaining a crystalline compound of Formula 1 by reacting a compound of Formula 2' with a compound of Formula 3' in Scheme 1-2 below and then performing a crystallization process; and (2) reacting the crystalline compound of Formula 1 with citric acid at 50 to 80° C. in one or more solvents selected from the group consisting of an organic solvent and water:

[Scheme 1-2]

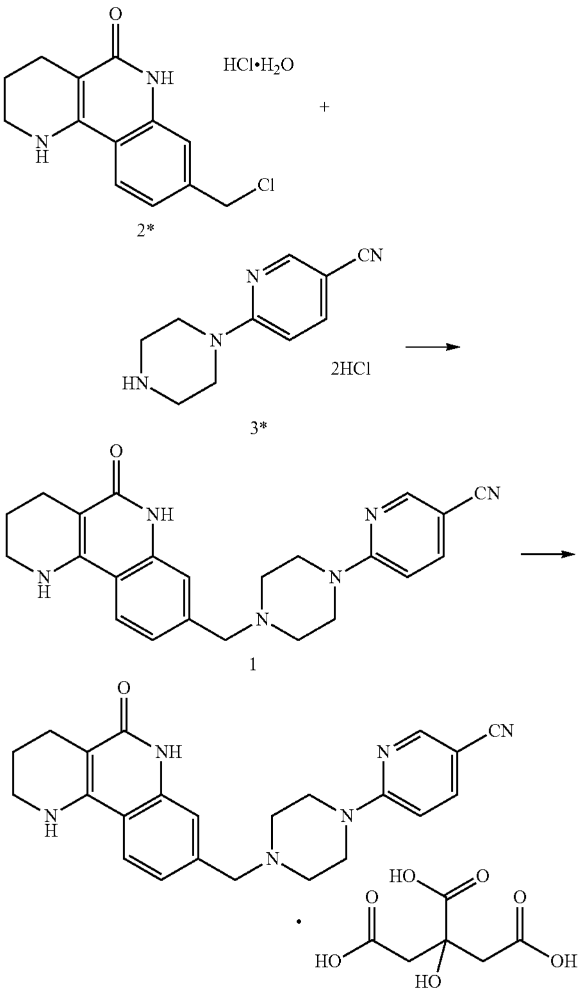

Steps (1) and (2) above may be performed in the same manner as steps (a) and (b) in the 1st method described above, except that a changed starting material is used.

On the other hand, when the crystalline form of the citrate of the tricyclic derivative compound is prepared as an anhydride in the 1st or 2nd method, the anhydride may be prepared in a crystalline form of the anhydride by adding a citrate to the tricyclic derivative compound represented by Formula 1 in step (b) or step (2) above, but as shown in Scheme 2 below, it may be prepared by preparing the compound of Formula 1 in a crystalline form of citrate monohydrate and then converting the crystalline form of the hydrate back to the crystalline form of anhydride.

[Scheme 2]

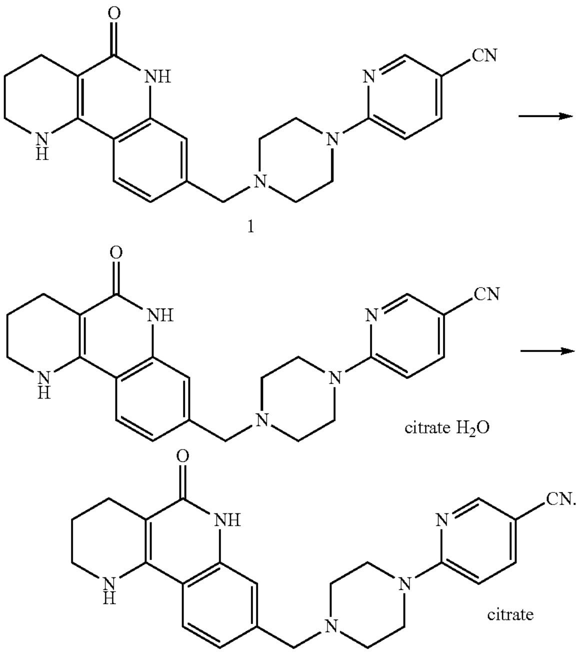

1

In Scheme 2 above, the process of converting monohydrate to anhydride may be performed by reacting monohydrate in an organic solvent or a mixed solvent of an organic solvent and water at a temperature of 50 to 80° C. In this case, a filtration process may be further performed.

In this case, at least one selected from ethanol, acetone, isopropanol, acetonitrile, propanol, butanol, ethyl acetate, and tetrahydrofuran may be used as the organic solvent.

In addition, when the mixed solvent is used, an advantageous effect of reducing the residual solvent level may be provided by containing a small amount of water.

Water to be included in the mixed solvent may be used in an amount of 2 to 15 parts by weight, preferably 4 to 8 parts by weight, based on 100 parts by weight of monohydrate. When the water is included in an amount of less than 2 parts by weight, it is difficult to obtain the above effect, and when it is included in an amount exceeding 15 parts by weight, conversion to an anhydride may not occur, which is not preferable.

In this way, when citrate anhydride is prepared from citrate hydrate, an effect in which related substances are additionally removed in the process of converting the crystalline form from the hydrate to the anhydride may be achieved, so that a higher purity compound may be obtained.

In the method for preparing the crystalline form of the citrate of the tricyclic derivative compound according to the present invention, the reaction in step (a) above may be performed without performing a reflux process, a recrystallization process may not be further performed after the crystallization process in step (a) above, and a column chromatography purification process may not be performed after the crystallization process in step (a) above.

According to the preparation method of the present invention, even if all of the reflux process, the recrystallization process and the tubular chromatography purification process are not performed, excellent yield and purity are provided, and the number of preparation processes may be greatly reduced.

In the preparation method, the compound of Formula 2 in Scheme 1-1 above may be prepared by including the steps of:

(a) reacting with hydrochloric acid after adding an organic solvent to the compound of Formula 4 in Scheme 3-1 below;

(b) adding an organic solvent and water to the reaction product in a volume ratio of 1:1 to 1:3; and (c) adjusting the pH of the reaction product in step (b) to 8 to 10 and then filtering:

[Scheme 3-1]

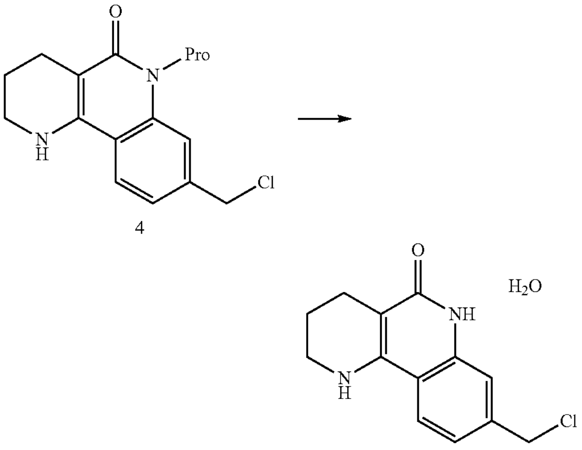

4

2

In Compound 4 above, "Pro" may be a protecting group selected from the group consisting of an aryl group, a benzyl group, a benzyloxymethyl group, a paramethoxybenzyl group (PMB) and a methoxymethyl group (MOM), preferably a methoxymethyl group.

In steps (a) and (b) above, at least one selected from ethanol, acetone, isopropanol, acetonitrile, propanol, butanol, ethyl acetate and tetrahydrofuran may be used as the organic solvent.

In step (c) above, pH adjustment may be performed using a base, and at least one selected from the group consisting of NaOH, KOH, $K_2CO_3$, $Na_2CO_3$, $NaHCO_3$, and the like may be used as the base.

In addition, in the preparation method, the compound of Formula 2' in Scheme 1-2 above may be prepared by comprising the steps of:

(1) reacting with hydrochloric acid after adding an organic solvent to the compound of Formula 4 in Scheme 3-2 below; and (2) adding an aqueous hydrochloric acid solution after completion of the reaction to the reaction solution and filtering:

[Scheme 3-2]

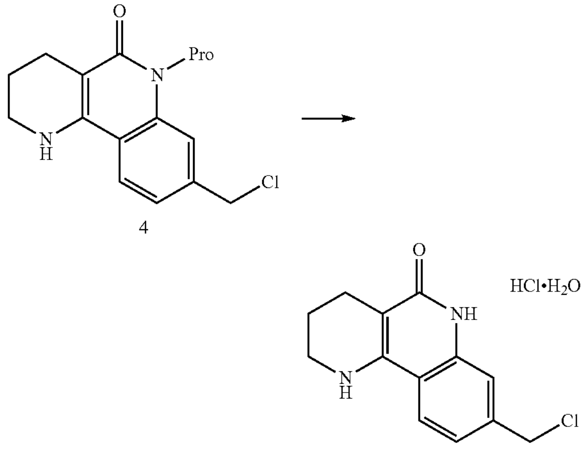

4

2*

In step (1) above, the reaction may be carried out at 75 to 85° C. In addition, the reaction may be carried out for 1 to 4 hours, preferably 2 to 3 hours, and in this case, stirring may also be performed.

In step (2) above, the addition of the aqueous hydrochloric acid solution may be performed after cooling the reaction solution, and the cooling temperature may be 10 to 40° C. Preferably, it may be 15 to 25° C.

The aqueous hydrochloric acid solution may be used at a volume concentration of 5 to 25%, preferably 10 to 20% of hydrochloric acid. The aqueous hydrochloric acid solution may be added in an amount of 0.1 to 6.5 parts by weight, preferably 1.5 to 4.5 parts by weight, based on 100 parts by weight of the starting material.

In step (1) above, at least one selected from ethanol, acetone, isopropanol, acetonitrile, propanol, butanol, ethyl acetate and tetrahydrofuran may be used as the organic solvent.

After step (2) above, at least one selected from isopropyl alcohol, purified water, and the like may be preferably used for washing.

Pharmaceutical Composition Comprising a Crystalline Form of a Citrate of a Tricyclic Derivative Compound, Use Thereof, and Treatment Method Using the Same The present invention provides a pharmaceutical composition for preventing or treating diseases caused by the activity of PARP-1, tankyrase-1 or tankyrase-2, comprising a crystalline form of a citrate of a tricyclic derivative compound represented by Formula 1 below as an active ingredient:

[Formula 1]

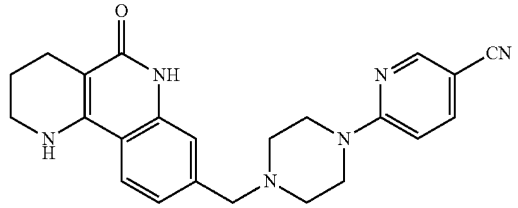

Diseases caused by the activity of PARP-1, tankyrase-1, or tankyrase-2 may include neuropathological pain, epilepsy, stroke, Alzheimer's disease, Parkinson's disease, amyotrophic lateral sclerosis (ALS), Huntington's disease, schizophrenia, chronic or acute pain, ischemic brain injury, neuronal loss after hypoxia, trauma and nerve injury, neurodegenerative disease, atherosclerosis, hyperlipidemia, cardiovascular diseases such as cardiovascular tissue damage, coronary artery disease, myocardial infarction, angina pectoris and cardiogenic shock, diabetic neuropathy, osteoarthritis, osteoporosis or cancer, and the like.

The crystalline form of the citrate of the tricyclic derivative compound of the present invention may be usefully used for preventing or treating diseases caused by the activity of PARP-1, tankyrase-1 or tankyrase-2, especially neuropathological pain, neurodegenerative diseases, cardiovascular diseases, diabetic neuropathy, inflammatory diseases, osteoporosis or cancer, by inhibiting the activity of poly(ADP-ribose) polymerase.

The cancer may be in the form of advanced solid cancer, recurrent solid cancer or metastatic solid cancer. The solid cancer may be, but is not limited to, breast cancer, prostate cancer, pancreatic cancer, ovarian cancer, advanced ovarian cancer, high-grade serous ovarian cancer (including fallopian tube cancer and primary peritoneal cancer), metastatic cancer metastasized from primary ovarian cancer, breast cancer, prostate cancer and pancreatic cancer.

Each of the compositions comprising the citrate of the tricyclic derivative compound of the present invention may be formulated and used in the form of oral formulations such as tablets, powders, granules, pills, capsules, suspensions, emulsions, solutions for internal use, emulsions and syrups, external preparations, suppositories or sterile injectable solutions according to conventional methods.

The pharmaceutical composition according to the present invention may further comprise one or more pharmaceutically acceptable carriers, one or more excipients and/or diluents.

Non-limiting examples of suitable pharmaceutically acceptable carriers include solids and/or liquids, for example, ethanol, glycerol, water, and the like. The amount of carriers in the therapeutic composition may range from about 5 to about 99% by weight based on the total weight of the therapeutic composition or therapeutic combination. Non-limiting examples of suitable pharmaceutically acceptable excipients and diluents include non-toxic compatible fillers, binders, disintegrants, buffers, preservatives, wetting agents, extenders, antioxidants, lubricants, flavoring agents, thickeners, colorants, surfactants, emulsifiers, suspending agents, and the like. Such excipients and diluents may be, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, or the like, and it will be apparent to those skilled in the art that all other pharmaceutically acceptable carriers, excipients and diluents may be used.

In the pharmaceutical composition of the present invention, the crystalline form of the citrate of the tricyclic derivative compound is contained in a therapeutically effective amount or a prophylactically effective amount. A preferable dosage of the citrate of the tricyclic derivative compound according to the present invention varies depending on the condition and body weight of the patient, the severity of the disease, the form of the drug, and the route and duration of administration, but may be appropriately selected by those skilled in the art. However, for the desired effect, the crystalline form of the citrate of the tricyclic derivative compound of the present invention may be administered in divided doses of 0.0001 mg to 1000 mg, 0.01 mg to 500 mg, 0.1 mg to 300 mg, 1 mg to 200 mg, or 50 mg to 200 mg once or several times a day. The compound of Formula 1 above in the composition of the present invention may be combined in an amount of 0.0001 to 50% by weight based on the total weight of the total composition.

In addition, the present invention provides the use of the crystalline form of the tricyclic derivative compound, the crystalline form of the citrate of the tricyclic derivative compound or the pharmaceutical composition for the preparation of a drug for preventing or treating various diseases caused by the activity of PARP-1, tankyrase-1 or tankyrase-2.

In addition, the present invention provides a method of treating an animal with the diseases described above, comprising administering to the animal an effective amount of the crystalline form of the tricyclic derivative compound, the crystalline form of the citrate of the tricyclic derivative compound or the pharmaceutical composition.

Advantageous Effects

The crystalline form of the citrate of the tricyclic derivative compound according to the present invention has an excellent inhibitory effect on the activity of PARP-1, tankyrase-1 or tankyrase-2, and thus, it may be usefully used for preventing or treating neuropathological pain, neurodegenerative diseases, cardiovascular diseases, diabetic neuropathy, inflammatory diseases, osteoporosis or cancer.

In addition, the crystalline form of the citrate of the tricyclic derivative compound according to the present invention has improved purity, solubility and stability, and thus, it provides an effect of facilitating the preparation of pharmaceutical formulations and improving storage stability.

The preparation method of the present invention provides a compound having excellent yield and purity, and remarkably improves preparation efficiency by simplifying the preparation process, and thus, it provides a method that is commercially very useful while enabling mass production.

DESCRIPTION OF DRAWINGS

FIG. 1 is a graph illustrating peaks in the XRD analysis of the compound of Formula 1 (anhydride) prepared in Example 1, FIG. 2 is a graph illustrating endothermic peaks in the DSC analysis of the compound of Formula 1 (anhydride) prepared in Example 1, FIG. 3 is a graph illustrating the results of TGA analysis of the compound of Formula 1 (anhydride) prepared in Example 1, FIG. 4 is a graph illustrating peaks in the XRD analysis of the compounds of Formula 1 (dihydrate) prepared in Examples 1-4, FIG. 5 is a graph illustrating endothermic peaks in the DSC analysis of the compounds of Formula 1 (dihydrate) prepared in Examples 1-4, FIG. 6 is a graph illustrating the results of TGA analysis of the compounds of Formula 1 (dihydrate) prepared in Examples 1-4;

FIG. 7 is a graph illustrating peaks in the XRD analysis of the citrate of the compound of Formula 1 (anhydride) prepared in Example 2, FIG. 8 is a graph illustrating endothermic peaks in the DSC analysis of the citrate of the compound of Formula 1 (anhydride) prepared in Example 2, FIG. 9 is a graph illustrating the results of TGA analysis of the citrate of the compound of Formula 1 (anhydride) prepared in Example 2, FIG. 10 is a graph illustrating peaks in the XRD analysis of the citrate of the compound of Formula 1 (monohydrate) prepared in Example 3, FIG. 11 is a graph illustrating endothermic peaks in the DSC analysis of the citrate of the compound of Formula 1 (monohydrate) prepared in Example 3, FIG. 12 is a graph illustrating the results of TGA analysis of the citrate of the compound of Formula 1 (monohydrate) prepared in Example 3, FIG. 13 is a graph illustrating peaks in the XRD analysis of the citrate of the compound of Formula 1 (dihydrate) prepared in Example 4, FIG. 14 is a graph illustrating endothermic peaks in the DSC analysis of the citrate of the compound of Formula 1 (dihydrate) prepared in Example 4, FIG. 15 is a graph illustrating the results of TGA analysis of the citrate of the compound of Formula 1 (dihydrate) prepared in Example 4, FIG. 16 is a graph illustrating the results of measuring the PARP-1 enzyme inhibitory activity of the crystalline form of the citrate anhydride of the compound of Formula 1 of the present invention and conventional drugs, FIG. 17 is a graph illustrating the results of measuring the tankyrase-1 enzyme inhibitory activity of the citrate anhydride of the compound of Formula 1 of the present invention and conventional drugs, and FIG. 18 is a graph illustrating the results of measuring the tankyrase-2 enzyme inhibitory activity of the citrate anhydride of the compound of Formula 1 of the present invention and conventional drugs.

BEST MODE

Hereinafter, the present invention will be described in more detail through examples. It will be apparent to those skilled in the art that these examples are only for illustrating the present invention and the scope of the present invention is not to be construed as being limited to these examples.

Preparative Example 1: Preparation of Compound 2

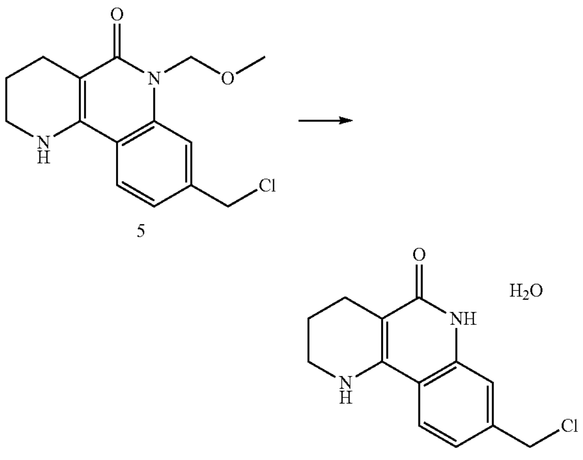

5

2

46.7 L of ethanol was added to Compound 5 (4.5 kg, 15.37 mol), and then c-HCl (5.3 L, 61.48 mol) was added thereto. After stirring under reflux for 2 hours and confirming the completion of the reaction, it was cooled and 16 L of ethanol and 29.4 L of purified water were added thereto. The pH was adjusted to 8 to 10 with 6 N aqueous NaOH solution, and then filtered to obtain Compound 2 (3.46 kg, yield of 84.4%).

Preparative Example 2: Preparation of Compound 2'

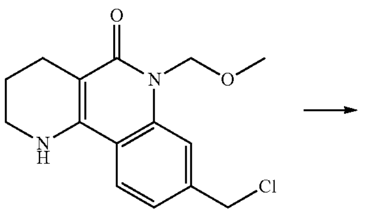

5

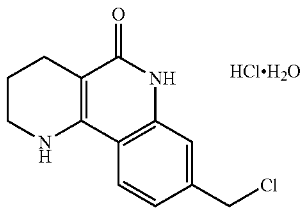

2'

Isopropanol (6813 mL) was added to Compound 5 (681.3 g, 2.33 mol), and then c-HCl (970 g, 9.32 mol) was added thereto. It was stirred for 2 to 3 hours at 75 to 85° C. After confirming the completion of the reaction, it was cooled and a 6 N aqueous HCl solution was added thereto. The resulting solid was filtered to obtain Compound 2' (600 g, yield of 85.1%).

Example 1: Synthesis of 6-{4-[(5-oxo-1,2,3,4,5,6-hexahydrobenzo[h][1,6]naphthyridin-8-yl)methyl]piperazin-1-yl}nicotinonitrile (Free Form)

(1) Example 1-1

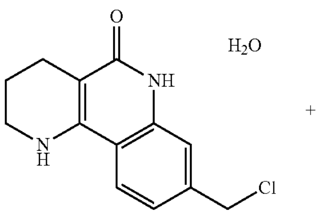

2

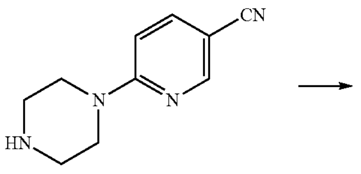

3

-continued

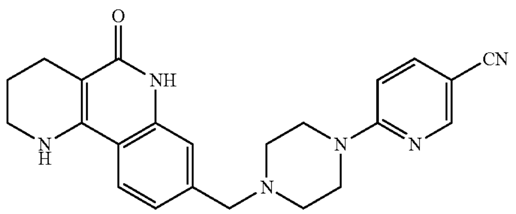

1

DMF (65 L) was added to Compound 2 (6.5 kg, 24.37 mol) and Compound 3 (5.73 kg, 30.46 mol). Triethylamine (2.71 kg, 26.8 mol) was added thereto and stirred at 45 to 50° C. for 5 hours. After confirming the completion of the reaction, it was cooled and crystallized by the addition of methanol (130 L). The resulting solid was filtered. 65 L of methanol was added to the wet solid and stirred under reflux for 1.5 hours. After cooling, it was filtered to obtain Compound 1 (7.34 kg, yield of 75.2%).

(2) Example 1-2

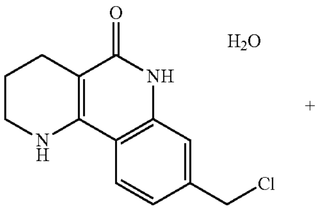

2

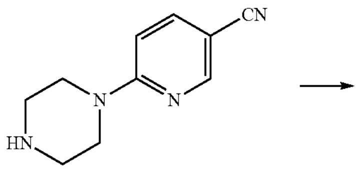

3

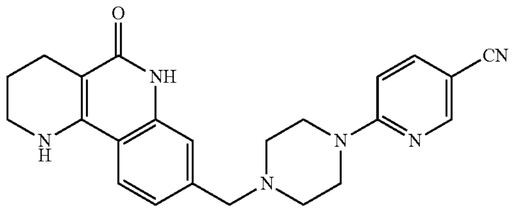

1

DMF (100 mL) was added to Compound 2 (10 g, 37.49 mmol) and Compound 3 (8.47 g, 44.99 mmol). Triethylamine (5.75 g, 41.24 mmol) was added thereto and stirred at 38 to 42° C. for 6 hours. After confirming the completion of the reaction, it was cooled and crystallized by the addition of purified water (100 mL). The resulting solid was filtered to obtain Compound 1 (13.99 g, yield of 93%).

(3) Example 1-3

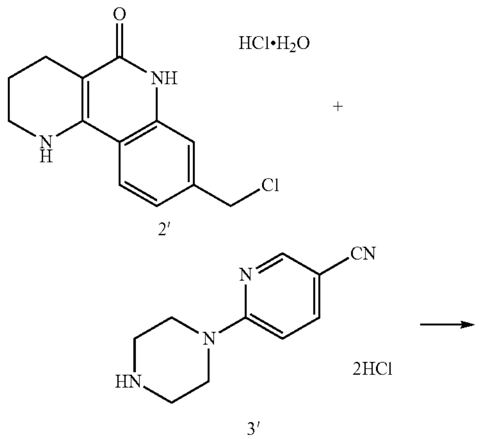

$HCl \cdot H_2O$

2'

3'

2HCl

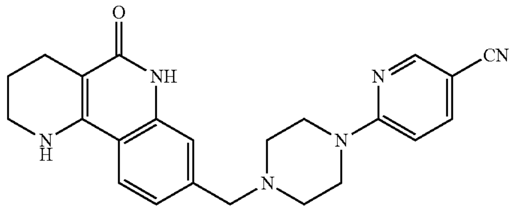

1

DMF (9.96 L) was added to Compound 3' (750.34 g, 2.87 mol), and then triethylamine (1097 g, 10.84 mol) was added thereto and stirred for 2 hours. Compound 2' (664.3 g, 2.19 mol) was added thereto and stirred at 45 to 50° C. for 5.5 hours. After confirming the completion of the reaction, it was cooled and crystallized by the addition of purified water (19.93 L). The resulting solid was filtered to obtain an anhydrous crystal of Compound 1 (788.41 g, yield of 89.9%).

(4) Example 1-4

Compound 1 (100 g, 249.7 mmol) prepared in Examples 1-1 to 1-3 was added to a mixed solvent of DMAC (1.6 L) and THE (1.6 L), and then dissolved by stirring at 45 to 55° C. After filtering, purified water (3.2 L) was added and cooled to 0 to 10° C. Through a process of stirring and filtering at the same temperature, a dihydrate crystal of Compound 1 was obtained.

As shown in FIGS. 1 to 3, it was confirmed that Compound 1 prepared in Examples 1-1 to 1-3 showed peaks at 2θ values of 7.88°, 10.23°, 13.89°, 15.16°, 15.78°, 18.05°, 19.27°, 19.51°, 22.79° and 23.94° in the X-ray diffraction (XRD) analysis (FIG. 1), and the endothermic peak was observed at 272° C. in the differential scanning calorimetry (DSC) analysis (FIG. 2). In addition, as a result of thermogravimetric analysis (TGA), it was confirmed to be an anhydrous crystalline form because no mass loss was initially observed (FIG. 3).

It was confirmed that the dihydrate crystal of Compound 1 further prepared in Example 1-4 above showed peaks at 2θ values of 7.95°, 10.25°, 13.25°, 13.78°, 21.12° and 25.22° in the X-ray diffraction (XRD) analysis (FIG. 4), and the endothermic peaks was observed at 117° C. and 272° C. in the differential scanning calorimetry (DSC) analysis (FIG. 5). In addition, as a result of thermogravimetric analysis (TGA), it was confirmed to be a dihydrate because a mass loss of about 7.7% was observed at around 94° C. (FIG. 6).

Example 2: Synthesis of Citrate Anhydride of 6-{4-[(5-oxo-1, 2, 3, 4, 5, 6-hexahydrobenzo[h][1,6]naphthyridin-8-yl)methyl]piperazine-1-yl}nicotinonitrile (1) Example 2-1

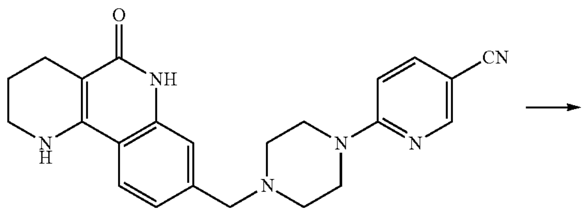

1

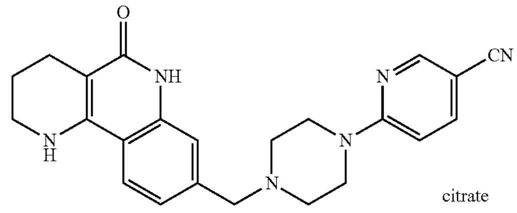

citrate

Ethanol (7.2 L) and methanol (2.4 L) were added to citric acid (690.8 g, 3.59 mol). Compound 1 (960 g, 2.39 mol) prepared in Example 1 above was added thereto and stirred at 65 to 70° C. for 2 hours. After cooling to room temperature, it was filtered. Methanol (7.2 L) was added to the wet solid and stirred under reflux for 2 hours. After cooling, it was filtered to obtain the target compound (1.31 kg, 92%).

(2) Example 2-2

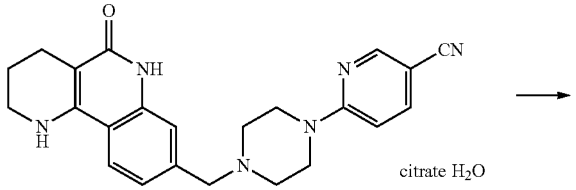

citrate $H_2O$

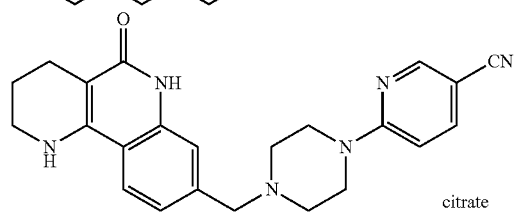

citrate

Ethanol (15.5 L), acetone (15.5 L) and isopropanol (15.5 L) were added to citrate of 6-{4-[(5-oxo-1, 2, 3, 4, 5, 6-hexahydrobenzo[h][1,6]naphthyridin-8-yl)methyl]piperazin-1-yl}nicotinonitrile (monohydrate) (4.7 kg, 7.7 mol) prepared in Example 3 below. After elevating the temperature to 55° C., it was stirred at 55 to 70° C. for 4 hours. After cooling to 25° C. or less, it was stirred for 30 minutes. The resulting solid was filtered to obtain a crystalline form of the target compound (4.39 kg, yield of 96.3%).

(3) Example 2-3

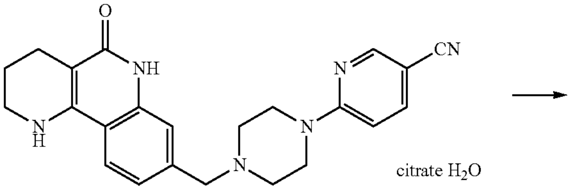

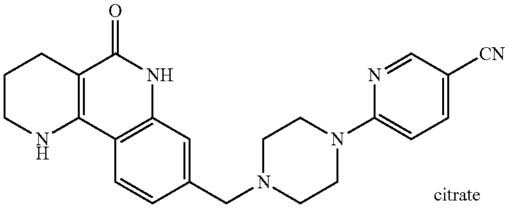

Ethanol (2.5 L), acetone (2.5 L) and isopropanol (2.5 L) were added to citrate of 6-{4-[(5-oxo-1, 2, 3, 4, 5, 6-hexahydrobenzo[h][1,6]naphthyridin-8-yl)methyl]piperazin-1-yl}nicotinonitrile (monohydrate) (500 g, 0.82 mol) prepared in Example 3 below, and purified water (20 mL) was added thereto. After elevating the temperature to 55° C., it was stirred at 55 to 75° C. for 4 hours. After cooling to 25° C. or less, it was stirred for 30 minutes. The resulting solid was filtered to obtain a crystalline form of the target compound (470 g, yield of 96.7%).

As shown in FIGS. 7 to 9, the crystalline compound of the citrate anhydride of Formula 1 showed peaks at 2θ values of 9.79°, 10.01°, 15.86°, 19.62°, 20.10°, 21.71° and 26.58° in the XRD analysis (FIG. 7), and endothermic peaks were observed at 230° C. and 270° C. in the DSC analysis (FIG. 8). In addition, as a result of TGA, it was confirmed to be an anhydride because no mass loss was initially observed (FIG. 9).

The methods of Example 2-2 and Example 2-3 showed an effect in which related substances were additionally removed in the process of converting from hydrate to anhydride, so that a higher purity anhydrous crystalline compound could be obtained.

Example 3: Synthesis of Citrate Monohydrate of 6-{4-[(5-oxo-1, 2, 3, 4, 5, 6-hexahydrobenzo[h][1, 6]naphthyridin-8-yl)methyl]piperazine-1-yl}nicotinonitrile

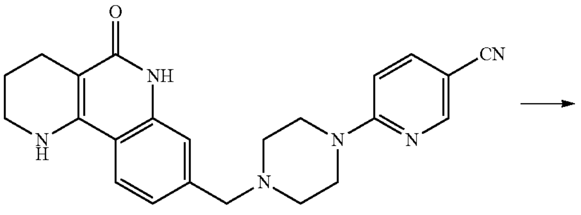

1

-continued

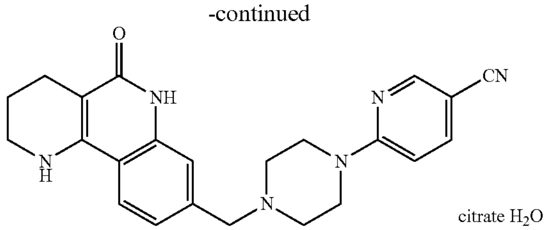

Methanol (25.7 L) and purified water (25.7 L) were added to Compound 1 (7.34 kg, 18.32 mol) prepared in Example 1 above. Citric acid (5.28 kg, 27.49 mol) dissolved in a 1:1 mixed solution (22 L) of methanol and purified water was added thereto. After stirring at 15 to 25° C. for 30 minutes, the temperature was elevated to 60° C., and stirred at 60 to 70° C. for 2 hours. After cooling to room temperature, it was filtered to obtain the target compound (10.7 kg, 95.8%).

As shown in FIGS. 10 to 12, the crystalline compound of the citrate monohydrate of Formula 1 showed peaks at 2θ values of 6.94°, 9.99°, 11.89°, 13.35°, 15.07°, 16.57°, 18.17°, 20.90°, 23.68° and 26.39° in the XRD analysis (FIG. 10), and endothermic peaks were observed at 120° C. and 193° C. in the DSC analysis (FIG. 11). In addition, as a result of TGA, it was confirmed to be a monohydrate because a mass loss of about 2.4% at 80 to 120° C. (FIG. 12).

In the preparation method, the target compound is obtained in crystalline form as the reaction is completed. Thus, recrystallization to increase purity or an additional process to reduce residual solvent is not required.

Example 4: Synthesis of Citrate Dihydrate of 6-{4-[(5-oxo-1, 2, 3, 4, 5, 6-hexahydrobenzo[h][1,6]naphthyridin-8-yl)methyl]piperazine-1-yl}nicotinonitrile

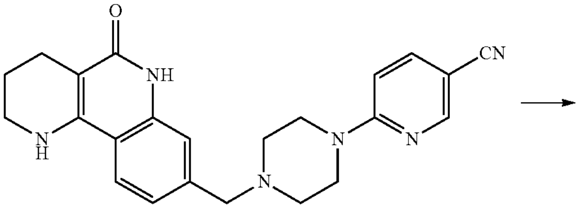

1

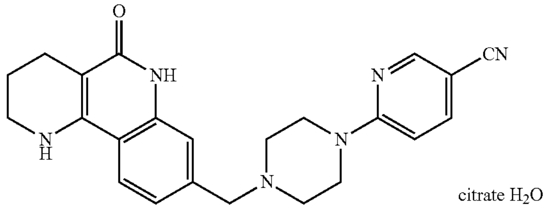

Purified water (42 mL) was added to Compound 1 (6 g, 15 mmol) prepared in Example 1 above. Citric acid (3.6 g, 22.5 mmol) dissolved in purified water (18 mL) was added thereto. After stirring at room temperature for 30 minutes, the temperature was elevated to 60° C., and stirred at 60-65° C. for 1.5 hours. After cooling to room temperature, it was filtered to obtain the target compound (8.45 g, yield of 97.8%).

As shown in FIGS. 13 to 15, the crystalline compound of the citrate dihydrate of Formula 1 showed peaks at 2θ values of 8.15°, 10.96°, 13.35°, 16.09°, 18.73°, 21.47°, 25.45°, 26.86°, and 28.51° in the XRD analysis (FIG. 13), and endothermic peaks were observed at 140° C., 176° C. and 266° C. in the DSC analysis (FIG. 14). In addition, as a result of TGA, it was confirmed to be a dihydrate because a mass loss of about 5.6% at 100 to 150° C. (FIG. 15).

Comparative Examples 1: Synthesis of 6-{4-[(5-oxo-1,2, 3, 4, 5, 6-hexahydrobenzo[h][1,6]naphthyridin-8-yl)methyl]piperazin-1-yl}nicotinonitrile (Free Form)

(1) Comparative Synthesis Example 1-1

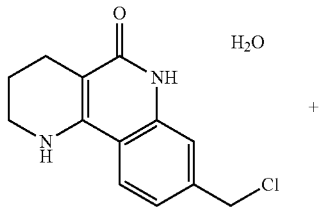

2

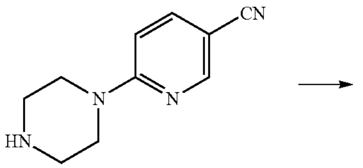

3

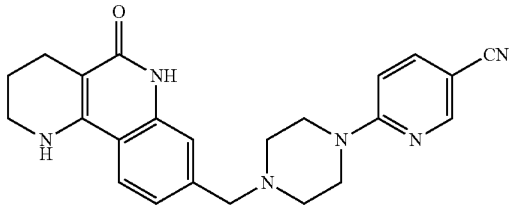

1

35.8 L of methanol was added to Compound 2 (2.56 kg, 9.6 mol) and Compound 3 (1.98 kg, 10.56 mol). Triethylamine (2.67 L, 19.2 mol) was added thereto and stirred under reflux for 24 hours. After confirming the completion of the reaction, DMAC (38.4 L) and THF (38.4 L) were added thereto, and dissolved by elevating the temperature. Activated carbon was added to the solution and stirred. After filtration, it was added dropwise to purified water to crystallize and filtered.

DMAC and THE were added to the wet solid and dissolved, and then recrystallized to obtain Compound 1 (2.93 kg, 71.1%).

(Step 1)

Thereafter, an additional purification process was performed to remove related substances to obtain clean Compound 1 (1.59 kg, yield of 39%). (Step 2)

(2) Comparative Synthesis Example 1-2

(Step a)

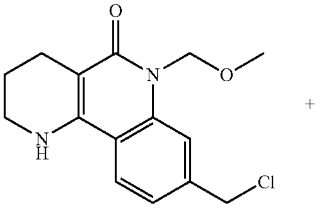

5

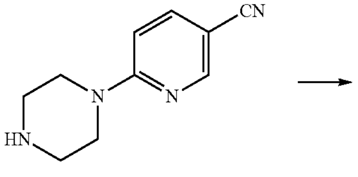

3

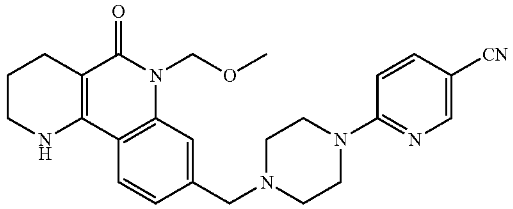

Methanol was added to Compound 5 above, and then 6-(piperazin-1-yl) nicotinonitrile and triethylamine were added thereto. After stirring at 80° C. for 24 hours and confirming the completion of the reaction, the reaction solution was concentrated. Thereafter, it was extracted with dichloromethane, the organic solvent layer was dried over anhydrous magnesium sulfate, and the solvent was concentrated under reduced pressure to obtain a residue, which was purified by column chromatography (hexane:ethyl acetate=1:9) to obtain a compound (yield of 75%) similar to the scheme above.

(Step b)

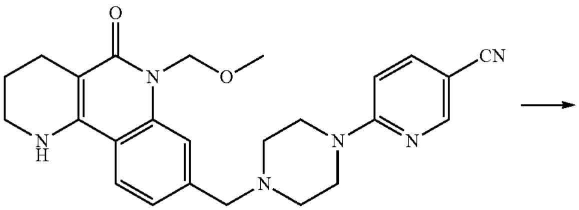

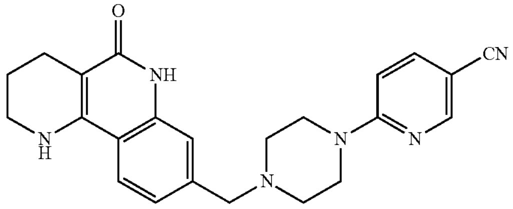

1

The compound prepared in step a was dissolved in dichloromethane, and then trifluoroacetic acid was added thereto and heated for 24 hours using a reflux condenser. After confirming the completion of the reaction, it was extracted with dichloromethane and extracted with dichloromethane once more in a saturated aqueous sodium hydrogen carbonate solution. It was dried over anhydrous magnesium sulfate, and the solvent was concentrated under reduced pressure to obtain a residue, which was purified by column chromatography (dichloromethane:methanol=1:9) to obtain the compound of Formula 1 (yield of 65%).

Comparative Examples 2: Synthesis of Dichloride Salt of 6-{4-[(5-oxo-1,2, 3, 4, 5, 6-hexahydrobenzo [h][1,6]naphthyridin-8-yl)methyl]piperazine-1-yl}nicotinonitrile

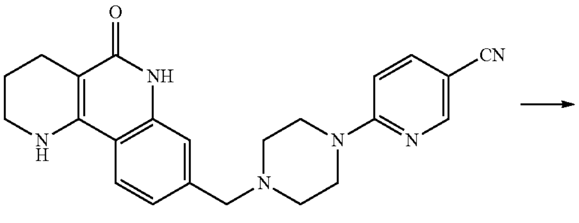

1

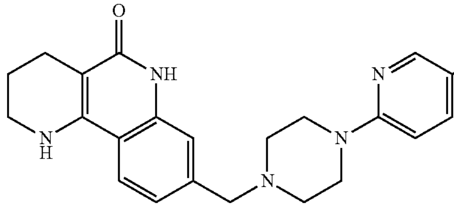

2HCl

Compound 1 obtained in Comparative Synthesis Example 1-2 above was dissolved in methanol, and then 1.25 M hydrochloric acid methanol solution was added thereto and stirred for 12 hours. After completion of the reaction, the solvent was concentrated under reduced pressure, and then the solid was filtered with ethyl acetate to obtain the dihydrochloride salt of Compound 1 (yield of 95%).

Analytical Method: Moisture Content, DSC, TGA and XRD Analysis

Moisture content, DSC, TGA and XRD analysis described in the present invention were conducted in the following manner:

(1) Moisture Content Measurement

Moisture content was measured using an 870 KF Titrino Plus (Metrohm) Karl-Fisher moisture titrator.

(2) DSC Analysis

DSC analysis was performed on a DSC 8000 (PerkinElmer) analyzer at 30 to 250 to 350° C. A 0.5 to 2 mg of sample was weighed into an aluminum DSC pan and sealed non-hermetically with a perforated aluminum lid, and then the sample was heated from 30° C. to 250 to 350° C. at a scan rate of 10° C./min, and the resulting heat flow reaction was monitored.

(3) TGA Analysis

TGA analysis was performed on a TGA 8000 (PerkinElmer) analyzer at 30 to 900° C. A 0.5 to 2 mg of sample was weighed into a ceramic crucible, the sample was heated from 30° C. to 900° C. at a scan rate of 5° C./min, and the resulting mass loss was monitored.

(4) XRD Analysis

XRD analysis was performed on a D8 Focus (Bruker ASX) analyzer from 2° 2θ to 40° 2θ. An about 100 mg of sample was gently pressed onto the plastic sample holder so that the sample surface was smooth and just above the level of the sample holder, and then measured under the following conditions.

<Analysis Conditions>

Anode material (Ka): Cu Ka (1.5406 Å); scan range: 2 to 40°; generator settings: 40 mA, 40 kV; scan rate: 10°/min; divergence slit size: 0.6 mm; temperature: 25° C.; step size: 0.02° 2θ; rotation: used Experimental Example 1: Analysis of Related Substances The amounts of related substances included in the compounds prepared in the Examples and Comparative Examples above were measured using HPLC (product name: Agilent 1100; manufacturer: Agilent), and the results are shown in Table 2 below.

<HPLC Operating Conditions>

Detector: UV detector (detection wavelength: 220 nm)

Column: Watchers 100 ODS-P, 4.6×250 mm, 5 μm, or equivalent column

Temperature: constant temperature around 25° C.

Mobile phase A: prepared by dissolving 11.503 g of ammonium dihydrophosphate in 1000 mL of water and degassing after filtering, Mobile phase B: acetonitrile Mobile phase gradient:

TABLE 1

| Analysis time (min) | Mobile phase A (%) | Mobile phase B (%) |
|---|---|---|
| 0 | 85 | 15 |
| 5 | 80 | 20 |
| 15 | 80 | 20 |
| 20 | 75 | 25 |
| 25 | 75 | 25 |
| 75 | 30 | 70 |
| 76 | 85 | 15 |
| 90 | 85 | 15 |

Diluent: mobile phase A and acetonitrile mixed in a ratio of 5:5 are used.
Flow rate: 1.0 mL/min;
injection volume: 10.0 μL;
analysis time: 90 min
* Preparation of test solution: 10 mg of sample dissolved in 50 mL of diluent is used.

TABLE 2

| Analysis of related substances in the crystal (free form) of Compound 1 | | | | | |
|---|---|---|---|---|---|
| Compound 1 prepared in Comparative Synthesis Example 1-1 (Step 1) | | Compound 1 prepared in Comparative Synthesis Example 1-1 (Step 2) | | Compound 1 prepared in Example 1-2 | |
| RT (min) | Area (%) | RT (min) | Area (%) | RT (min) | Area (%) |
| 43.884 | 0.2435 | 44.006 | 0.0530 | — | — |
| 49.185 | 0.2475 | 48.987 | 0.1655 | 48.734 | 0.0225 |

TABLE 2-continued

| Analysis of related substances in the crystal of citrate of Compound 1 | | | |
|---|---|---|---|
| Crystal of citrate of Compound 1 prepared in Example 3 | | Crystal of citrate of Compound 1 prepared in Example 2-3 | |
| RT (min) | Area (%) | RT (min) | Area (%) |
| — | — | — | — |
| 48.843 | 0.0122 | — | — |

As a result of the above experiment, in the case of the crystalline form of citrate of Compound 1 prepared according to the Examples of the present invention, it was confirmed that although no recrystallization process was performed throughout the entire preparation process, major related substances were remarkably reduced or not detected.

In the case of HPLC analysis, related substances coming out around the retention time of 49 min are predicted to be substances generated due to an overreaction in the coupling process of Formulas 2 and 3 above, or Formulas 5 and 3 above, and it is difficult to separate and remove after generation, and thus, it is very important to reduce the related substances in the preparation process.

Related Substances Around RT 49:

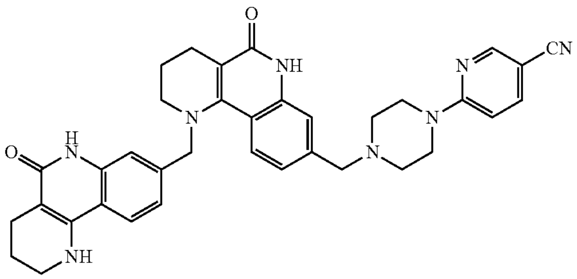 [SMILES: N#Cc1ccc(N2CCN(Cc3ccc4c5c(c(=O)[nH]c4c3)CCCN5Cc3ccc4c5c(c(=O)[nH]c4c3)CCCN5)CC2)nc1]

Experimental Example 2: Measurement of Solubility in Water

The solubility of the addition salt of Compound 1 in water was measured, and the results are shown in Table 4 below.

Specifically, an excess amount of the compound and solvent (10 mM, in 1 mL of water) were put into a shake-flask and shaken for 24 hours, and then quantitatively analyzed using UPLC.

<Equipment and Conditions Used>

Equipment name: Acquity UPLC (Waters)

Column: ACQUITY UPLC BEH C18 1.7 um×2.1 mm×50 mm

Wavelength: 226, 276, 310 nm (PDA detector)

Column temperature: 40° C.; sample temperature: 25° C.; injection volume: 5 ul

Mobile Phase and Concentration Gradient

TABLE 3

| Time (min) | Water (0.2% phosphoric acid) | Acetonitrile |
|---|---|---|
| 0 | 90 | 10 |
| 0.3 | 90 | 10 |
| 1.5 | 1 | 99 |
| 1.6 | 0 | 100 |

TABLE 3-continued

| Time (min) | Water (0.2% phosphoric acid) | Acetonitrile |
|---|---|---|
| 1.8 | 90 | 10 |
| 3.0 | 90 | 10 |

Compounds are dissolved in DMSO and measured by UPLC, and then a calibration curve is drawn.

The compounds saturated by the Shake-flask method are filtered and then measured by UPLC, and it is substituted into a calibration curve to calculate the concentration.

TABLE 4

| Salt | Water solubility (mM) | Salt | Water solubility (mM) |
|---|---|---|---|
| Crystalline anhydride of citrate of Compound 1 | 1.067 | Crystalline anhydride of succinic acid salt of Compound 1 | 0.498 |
| Crystalline anhydride of tartaric acid salt of Compound 1 | 0.241 | Crystalline anhydride of fumaric acid salt of Compound 1 | 0.444 |
| Crystalline anhydride of 2HCl salt of Compound 1 | 0.392 | Crystal (free form) of the compound of Formula 1 in Comparative Example 1-1 | 0.001 |

As a result of the above experiment, it was confirmed that the crystalline anhydride of citrate of Compound 1 of the present invention had remarkably excellent solubility in water compared to other salts.

Experimental Example 3: Confirmation of the Stability of the Addition Salt of Compound 1

The stability of crystals of the addition salt of Compound 1 prepared in the Examples and Comparative Examples above was confirmed, and the results are shown in Table 5 below.

Experiments according to temperature, humidity and light conditions were carried out by a method of confirming purity by HPLC after storage in a stability chamber under each condition.

<UV 200 Watt Irradiation>

Each sample was spread thinly in a Petri dish, and then the stability was evaluated after irradiation with UV light having a light intensity of 35 W to a total irradiation amount of 200 watts under conditions of 25° C. and 60% humidity using a photostability test chamber (CARON 6542-2).

<Visible 1200 k Lux Irradiation>

Each sample was spread thinly in a Petri dish, and then the stability was evaluated after irradiation with visible light having a light intensity of 35 k Lux to a total irradiation amount of 1200 k lux under conditions of 25° C. and 60% humidity using a photostability test chamber (CARON 6542-2).

TABLE 5

| Condition | Purity (%) Crystalline anhydride of 2HCl salt in Comparative Example 2 | Crystalline anhydride of citrate in Example 2 |
|---|---|---|
| Initial value | 97.89 | 97.97 |
| Temperature of 50 °C, 3 days | 97.79 | 97.86 |
| Humidity of 75%, 3 days | 97.76 | 97.81 |
| Temperature of 40 °C, humidity of 70%, 3 days | 97.83 | 97.79 |
| UV 200 watt - dark | 97.89 | 98.38 |
| UV 200 watt | 86.89 | 96.94 |
| Visible 1200k lux - dark | 97.89 | 98.39 |
| Visible 1200k lux | 93.40 | 96.73 |

As a result of the above experiment, both dihydrochloride and citrate anhydride of Compound 1 were found to be stable in the temperature and humidity. However, the dihydrochloride salt showed remarkably poor photostability at UV200 watt and Visible1200 k lux. If the photostability is low, storage stability may decrease by indoor lighting as well as sunlight, thereby lowering purity, and thus, care should be taken in management such as the need to store raw materials shaded. When the stability was confirmed in this way, the citrate of Compound 1 was found to be the most suitable.

Experimental Example 4: Confirmation of the Melting Point of a Salt

The melting points of the compounds of the citrate prepared in the Examples above were measured using a B-454 (BUCHI) melting point detector, and the results are shown in Table 6 below.

TABLE 6

| Crystalline anhydride of citrate in Example 2 | Crystalline monohydrate of citrate in Example 3 | Crystalline dihydrate of citrate in Example 4 |
|---|---|---|
| 206 °C | 176 °C | 173 °C |

As a result of the above experiment, it was confirmed that all of the crystalline forms of the citrate salt of the present invention had sufficiently high melting points as pharmaceutical raw materials.

Experimental Example 5: Measurement of Solubility in Various Solvents

The solubility of the crystalline compounds prepared in the Examples above in various solvents was measured, and the results are shown in Table 7 below.

Specifically, 0.1 g of sample was accurately weighed, put into each solvent, and shaken and mixed vigorously for 30 seconds every 5 minutes at 15 to 25° C., and the amount dissolved within 30 minutes was measured.

TABLE 7

| Solvent | Solubility (0.1 g/mL) Free form | Crystalline anhydride of citrate in Example 2 | Crystalline monohydrate of citrate in Example 3 | Crystalline dihydrate of citrate in Example 4 |
|---|---|---|---|---|
| DMF | 8 mL | 8 mL | 2.9 mL | 2.5 mL |
| MeOH | 300 mL | 100 mL or more | 9 mL | 9 mL |
| Aqueous HCl solution (pH 1.1) | 350 mL | 100 mL or less | 50 mL | 55 mL |
| EtOH | 1000 mL or more | 1000 mL or more | 350 mL | 450 mL |
| Water | 1200 mL or more | 1000 mL or less | 400 mL | 400 mL or more |

Experimental Example 6: Evaluation of Purity and Stability of Anhydride and Monohydrate of Citrate of Compound 1

The purity and stability of the crystalline anhydride of the citrate prepared in Example 2 and the crystalline monohydrate of the citrate prepared in Example 3 according to the present invention were evaluated, and the results are shown in Tables 8 and 9 below.

In the tables below, stability tests were conducted under accelerated storage conditions of a temperature of 40±2° C. and humidity of 75±5%, and purity and stability tests were conducted under long-term storage conditions of a temperature of 25±2° C. and humidity of 60±5%. Experimental results were measured under the same conditions as in Experimental Example 1 using HPLC (product name: agilent 1290, manufacturer: Agilent).

TABLE 8

| | (Standard %) Purity under accelerated storage conditions (period: month, area %) | | | | Purity under long-term storage conditions (period: month, area %) | | | |
|---|---|---|---|---|---|---|---|---|
| | Period | | | | | | | |
| | initial | 1 | 3 | 6 | initial | 1 | 3 | 6 |
| Crystalline anhydride of citrate in Example 2 (purity) | 99.66% | 99.64% | 99.65% | 99.54% | 99.66% | 99.64%<br>9<br>99.67%<br>24<br>99.74% | 99.66%<br>12<br>99.72%<br>36<br>99.73% | 99.58%<br>18<br>99.73% |

TABLE 9

| | (Standard %) | | | | | | |
|---|---|---|---|---|---|---|---|
| | Accelerated storage conditions (related substances) (period: month, area %) | | | Long-term storage conditions (related substances) (period: month, area %) | | | |
| | Period | | | | | | |
| | initial | 3 | 6 | initial | 3 | 6 | 9 |
| Crystalline anhydride of citrate in Example 2 | 0.26% | 0.24% | 0.28% | 0.26% | 0.28% | 0.29% | 0.31% |
| | | | | | 12 | 18 | 24 |
| | | | | | 0.29% | 0.33% | 0.34% |
| | | | | | 30 | 36 | |
| | | | | | 0.34% | 0.30% | |
| | Period | | | | | | |
| | initial | 3 | 6 | initial | 3 | 6 | |
| Crystalline monohydrate of citrate in Example 3 | 0.38% | 0.34% | 0.32% | 0.38% | 0.29% | 0.32% | — |

Experimental Example 7: Inhibition Test of Poly(ADP-Ribose) Polymerase [PARP-1] Enzyme The PARP-1 enzyme inhibitory activity of the crystalline anhydride of the citrate of the compound of Formula 1 (Example 2) according to the present invention and the crystalline anhydride of the hydrochloride salt of the compound of Formula 1 (Comparative Example 2) was assayed using a kit (cat. 80551) purchased from BPS Bioscience as follows.

Histones were coated on a 96-well plate provided from BPS Bioscience's kit and left at 4° C. for 16 hours. Thereafter, the plate was washed 4 times with PBST (7.5 mM $Na_2HPO_4$, 2.5 mM $NaH_2PO_4$, 145 mM NaCl, 0.05% Tween 20, pH 7.4), and then blocking buffer (provided from BPS Bioscience's kit) was added thereto to prevent non-specific reactions and left at 25° C. for 1 hour. After standing for 1 hour, the plate was washed 4 times with PBST, and various concentrations of the compounds of Example 2 and Comparative Example 2 were added to a reaction solution containing PARP-1 enzyme (50 ng/well), an assay mixture and an activated DNA, and reacted at 25° C. for 1 hour. After 1 hour, each well was washed 4 times with PBST, and streptavidin-linked peroxidase (Strep-HRP, 1:50 dilution) was added thereto to measure the amount of ribosylation by PARP enzyme, and reacted at 25° C. for 30 minutes. The plate was washed 4 times with PBST, and then HRP chemiluminescent substrate was finally added thereto and reacted. The amount of histone ribosylation formed by each enzyme was quantified using a Synergy™ H4 Hybrid Multi-Mode Microplate Reader (BioTek Instruments, Inc., US (A)). The results obtained for each concentration of the compounds of the present invention are the average values obtained in two wells, and the $IC_{50}$ values of the compounds were calculated using SigmaPlot 10 (Systat Software Inc., US (A)) for analysis of the results. AZD-2281 (Olaparib), which is a representative PARP inhibitor, was used as a control compound.

The experimental results are shown in Table 10 below, and are shown graphically in FIG. 16.

TABLE 10

| $IC_{50}$ | | |
|---|---|---|
| AZD-2281 (Olaparib) | Crystalline anhydride of dihydrochloride salt in Comparative Example 2 | Crystalline anhydride of citrate in Example 2 |
| 5.48 nM | 3.03 nM | 2.62 nM |

Experimental Example 8: Inhibition Test of Tankyrase-1 and Tankyrase-2 Enzymes The tankyrase-1 or tankyrase-2 enzyme inhibitory activity of the crystalline anhydride of the citrate of the compound of Formula 1 (Example 2) according to the present invention and the crystalline anhydride of the hydrochloride salt of the compound of Formula 1 (Comparative Example 2) was assayed as follows using kits (cat. 80573, 80578) purchased from BPS Bioscience:

Histones were coated on a 96-well plate provided from BPS Bioscience's kit and left at 4° C. for 16 hours. Thereafter, the plate was washed 4 times with PBST (7.5 mM $Na_2HPO_4$, 2.5 mM $NaH_2PO_4$, 145 mM NaCl, 0.05% Tween 20, pH 7.4), and then blocking buffer (provided from BPS Bioscience's kit) was added thereto to prevent non-specific reactions and left at 25° C. for 1 hour. After standing for 1 hour, the plate was washed 4 times with PBST, and various concentrations of the compounds of the Examples were added to a reaction solution containing tankyrase-1 enzyme (40 ng/well) or tankyrase-2 enzyme (15 ng/well) and an assay mixture, and reacted at 25° C. for 1 hour. After 1 hour, each well was washed 4 times with PBST, and streptavidin-linked peroxidase (Strep-HRP, 1:50 dilution) was added thereto to measure the amount of ribosylation by PARP enzyme, and reacted at 25° C. for 30 minutes. The plate was washed 4 times with PBST, and then HRP chemiluminescent substrate was finally added thereto and reacted. The amount of histone ribosylation formed by each enzyme was quantified using a Synergy™ H4 Hybrid Multi-Mode Microplate Reader (BioTek Instruments, Inc., US(A)). The results obtained for each concentration of the compounds of the present invention are the average values obtained in two wells, and the $IC_{50}$ values of the compounds were calculated using SigmaPlot 10 (Systat Software Inc., US (A)) for analysis of the results.

XAV-939, which is a representative tankyrase inhibitor, and BMN-673 (Talazoparib), which was developed as a PARP inhibitor but known to be effective in inhibiting tankyrases, were used as control compounds.

The experimental results are shown in Tables 11 and 12 below, and are shown graphically in FIGS. 17 and 18.

TABLE 11

| $IC_{50}$ | | |
|---|---|---|
| BMN-673 (Talazoparib) | XAV-939 | Anhydride of citrate in Example 2 |
| 8.29 nM | 8.22 nM | 4.31 nM |

TABLE 12

| $IC_{50}$ | | | |
|---|---|---|---|
| BMN-673 (Talazoparib) | XAV-939 | Crystalline anhydride of dihydrochloride salt in Comparative Example 2 | Crystalline anhydride of citrate in Example 2 |
| 2.53 nM | 2.21 nM | 1.12 nM | 1.06 nM |

The invention claimed is:

1. An anhydrous crystalline form of a citrate of a tricyclic derivative compound represented by the following formula:

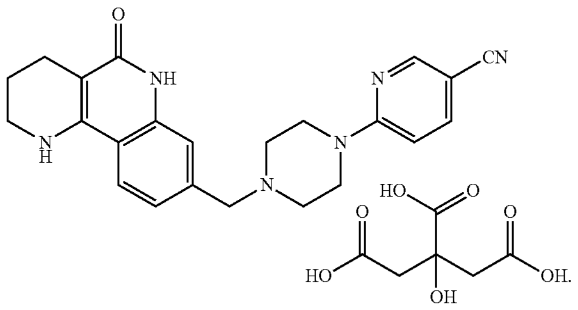

wherein the anhydrous crystalline form comprises 2θ(±0.2°) values of 10.01°, 15.86°, 19.62°, and 26.58° in a powder XRD pattern.

2. The anhydrous crystalline form according to claim 1, characterized in that the anhydrous crystalline form further comprises 2θ(±0.2°) values of 9.79°, 20.10°, and 21.71° in the powder XRD pattern.

3. A method for preparing the anhydrous a crystalline form according to claim 1, comprising:

reacting a crystalline compound of Formula 1 below with citric acid at 50 to 80° C. in an organic solvent to obtain the anhydrous crystalline form,

[Formula 1]

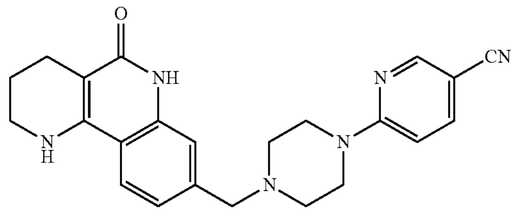

wherein the organic solvent is selected from the group consisting of methanol, ethanol, acetone, isopropanol, acetonitrile, butanol, propanol, tetrahydrofuran, and a mixture thereof.

4. The method for preparing the anhydrous crystalline form according to claim 3, characterized in that the organic solvent is a mixed solvent of methanol and ethanol.

* * * * *